US008845611B2

(12) United States Patent
Tsuruoka et al.

(10) Patent No.: US 8,845,611 B2
(45) Date of Patent: Sep. 30, 2014

(54) MULTI-CHAMBER BAG

(75) Inventors: Tatsuro Tsuruoka, Naruto (JP); Yasuhiro Ishikawa, Naruto (JP)

(73) Assignee: Otsuka Pharmaceutical Factory, Inc. (JP)

( * ) Notice: Subject to any disclaimer, the term of this patent is extended or adjusted under 35 U.S.C. 154(b) by 401 days.

(21) Appl. No.: 12/667,347

(22) PCT Filed: Jul. 16, 2008

(86) PCT No.: PCT/JP2008/062813

§ 371 (c)(1),
(2), (4) Date: Oct. 12, 2010

(87) PCT Pub. No.: WO2009/011359

PCT Pub. Date: Jan. 22, 2009

(65) Prior Publication Data

US 2011/0022022 A1 Jan. 27, 2011

(30) Foreign Application Priority Data

Jul. 19, 2007 (JP) ................................ 2007-188635

(51) Int. Cl.

| | |
|---|---|
| ***A61B 19/00*** | (2006.01) |
| ***B65D 81/32*** | (2006.01) |
| ***B65D 75/58*** | (2006.01) |
| ***B65D 81/26*** | (2006.01) |
| ***A61J 1/10*** | (2006.01) |
| *A61J 1/20* | (2006.01) |

(52) U.S. Cl.

CPC ........ *B65D 81/3266* (2013.01); *B65D 75/5883* (2013.01); *B65D 81/264* (2013.01); *A61J 2001/2024* (2013.01); *A61J 1/2093* (2013.01); *A61J 1/10* (2013.01)

USPC .......................................................... 604/410

(58) Field of Classification Search

USPC .......................................................... 604/410

See application file for complete search history.

(56) References Cited

U.S. PATENT DOCUMENTS 3,257,072 A * 6/1966 Reynolds ........................ 494/10
3,545,671 A * 12/1970 Ross ............................... 422/44

(Continued)

FOREIGN PATENT DOCUMENTS

CN 1062119 A 6/1992
CN 2860474 Y 1/2007

(Continued)

OTHER PUBLICATIONS

Egyptian Office Action (Egyptian Patent Appl. No. 16/2010) with its English translation.

(Continued)

*Primary Examiner* — Susan Su
*Assistant Examiner* — Guy K Townsend
(74) *Attorney, Agent, or Firm* — Berliner & Associates

(57) ABSTRACT

There is provided a multi-chamber bag that is capable of securely checking a medicinal substance accommodated therein without the necessity to perform a troublesome work, while preventing a matter deteriorating the medicinal substance from reaching the inside of a medicinal-substance accommodation chamber and hence securely preventing the deterioration of the medicinal substance. In a multi-chamber bag having a bag body that has a strong seal part that joins two sheet members together to define an interior space of the bag body, and a weak seal part that joints the two sheet members together so as to be able to rupture them apart, thereby partitioning the interior space of the bag body into a medicinal-substance accommodation chamber and a diluting-solution accommodation chamber, a pair of cover sheets are provided to respectively cover the medicinal-substance accommodation chamber. Each of the cover sheets is jointed to the facing sheet member so as to form an outside seal part surrounding the medicinal-substance accommodation chamber. One of the cover sheets has a structure capable of absorbing adverse influence causing matters, and a communication part for communication between spaces formed between both the sheet members and the both the cover sheets on both the sides is formed between an inside edge of the outside seal part and an inside edge of the strong seal part.

6 Claims, 23 Drawing Sheets

(56) References Cited

U.S. PATENT DOCUMENTS

| | | | | | |
|---|---|---|---|---|---|
| 3,608,709 | A | * | 9/1971 | Pike | 206/219 |
| 3,809,224 | A | * | 5/1974 | Greenwood | 206/219 |
| 4,396,383 | A | * | 8/1983 | Hart | 604/518 |
| 4,458,811 | A | * | 7/1984 | Wilkinson | 206/219 |
| 4,467,588 | A | * | 8/1984 | Carveth | 53/425 |
| 4,484,920 | A | * | 11/1984 | Kaufman et al. | 604/416 |
| 4,507,114 | A | * | 3/1985 | Bohman et al. | 604/111 |
| 4,614,267 | A | * | 9/1986 | Larkin | 206/221 |
| 4,619,650 | A | * | 10/1986 | Wisdom | 604/408 |
| 4,622,032 | A | * | 11/1986 | Katsura et al. | 604/122 |
| 4,629,080 | A | * | 12/1986 | Carveth | 215/11.1 |
| 4,711,359 | A | * | 12/1987 | White et al. | 215/11.1 |
| 4,994,056 | A | * | 2/1991 | Ikeda | 604/410 |
| 5,114,004 | A | * | 5/1992 | Isono et al. | 206/222 |
| 5,176,634 | A | * | 1/1993 | Smith et al. | 604/87 |
| 5,207,509 | A | * | 5/1993 | Herbert | 383/38 |
| 5,240,525 | A | * | 8/1993 | Percec et al. | 156/60 |
| 5,257,985 | A | * | 11/1993 | Puhl | 604/410 |
| 5,259,844 | A | * | 11/1993 | Bilstad et al. | 604/408 |
| 5,267,646 | A | * | 12/1993 | Inoue et al. | 206/204 |
| 5,287,961 | A | * | 2/1994 | Herran | 206/219 |
| 5,306,269 | A | * | 4/1994 | Lewis et al. | 604/403 |
| 5,423,421 | A | * | 6/1995 | Inoue et al. | 206/219 |
| 5,431,496 | A | * | 7/1995 | Balteau et al. | 383/38 |
| 5,458,244 | A | * | 10/1995 | Emori | 206/527 |
| 5,462,526 | A | * | 10/1995 | Barney et al. | 604/85 |
| 5,501,887 | A | * | 3/1996 | Tanaka et al. | 428/35.2 |
| 5,706,937 | A | * | 1/1998 | Futagawa et al. | 206/221 |
| 5,843,049 | A | * | 12/1998 | Heilmann et al. | 604/275 |
| 5,928,213 | A | * | 7/1999 | Barney et al. | 604/410 |
| 5,944,709 | A | | 8/1999 | Barney et al. | |
| 6,117,123 | A | * | 9/2000 | Barney et al. | 604/410 |
| 6,165,161 | A | * | 12/2000 | York et al. | 604/408 |
| 6,186,998 | B1 | * | 2/2001 | Inuzuka et al. | 604/410 |
| 6,203,535 | B1 | * | 3/2001 | Barney et al. | 604/408 |
| 6,231,559 | B1 | * | 5/2001 | Loretti | 604/410 |
| 6,364,864 | B1 | * | 4/2002 | Mohiuddin et al. | 604/410 |
| 6,468,259 | B1 | * | 10/2002 | Loretti et al. | 604/410 |
| 6,484,874 | B1 | * | 11/2002 | Kageyama et al. | 206/219 |
| 6,682,517 | B1 | * | 1/2004 | Ezaki et al. | 604/410 |
| 6,712,202 | B2 | * | 3/2004 | Muller et al. | 206/219 |
| 6,764,567 | B2 | * | 7/2004 | Sperko et al. | 156/229 |
| 6,846,305 | B2 | * | 1/2005 | Smith et al. | 604/410 |
| 6,996,951 | B2 | * | 2/2006 | Smith et al. | 53/425 |
| 7,207,970 | B2 | * | 4/2007 | Hasegawa | 604/90 |
| 7,243,787 | B2 | * | 7/2007 | Iwasa et al. | 206/219 |
| 7,658,279 | B2 | * | 2/2010 | Oka et al. | 206/219 |
| 2003/0047467 | A1 | * | 3/2003 | Smith et al. | 206/221 |
| 2004/0068960 | A1 | * | 4/2004 | Smith et al. | 53/396 |
| 2004/0137177 | A1 | * | 7/2004 | Saito et al. | 428/35.2 |
| 2004/0188281 | A1 | * | 9/2004 | Iwasa et al. | 206/219 |
| 2005/0087456 | A1 | * | 4/2005 | Oka et al. | 206/219 |
| 2007/0123836 | A1 | * | 5/2007 | Fukushima et al. | 604/410 |
| 2008/0255535 | A1 | * | 10/2008 | Yoshikawa | 604/410 |
| 2009/0209935 | A1 | * | 8/2009 | Inoue et al. | 604/416 |
| 2009/0299324 | A1 | * | 12/2009 | Inoue et al. | 604/410 |

FOREIGN PATENT DOCUMENTS

| | | | |
|---|---|---|---|
| JP | 11-056970 | | 3/1999 |
| JP | 2005-028167 | | 2/2005 |
| JP | 3131605 | | 5/2007 |
| JP | D121042 | | 1/2008 |
| TW | 384221 | B | 3/2000 |
| WO | 2000/074746 | A1 | 12/2000 |
| WO | WO2007/063638 | | 6/2007 |
| WO | WO2007/063777 | A1 | 6/2007 |
| WO | 2007/113963 | A1 | 10/2007 |

OTHER PUBLICATIONS

European Search Report dated Oct. 9, 2012 issued in connection with corresponding European Patent Appl. No. 08791208.5.

Taiwanese corresponding Application No. 097127191 Office Action issued Feb. 26, 2013.

* cited by examiner

MULTI-CHAMBER BAG

FIELD OF THE INVENTION

The present invention relates to a multi-chamber bag, in which a medicinal-substance accommodation chamber for accommodating a medicinal substance and a medicinal-solution accommodation chamber for accommodating a medicinal solution are formed independently of each other.

BACKGROUND OF THE INVENTION

Hitherto, there is known a multi-chamber bag that has a bag body, in which at least a medicinal-substance accommodation chamber for accommodating a powdered or liquid medicinal substance, and a medicinal-solution accommodation chamber for accommodating a medicinal solution, such as diluting solution, are formed.

The bag body has a strong seal part that joins two overlapped sheet members together, thereby defining an interior space, and a weak seal part that separably joins the sheet members together, thereby partitioning the interior space into the medicinal-substance accommodation chamber and the medicinal-solution accommodation chamber. With the multi-chamber bag having this structure, the two sheet members of the bag body are separated from each other through the weak seal part, thereby bringing the medicinal-substance accommodation chamber and the medicinal-solution accommodation chamber into communication with each other and hence mixing the medicinal substance and the medicinal solution together.

Taking into account the fear that adverse influence causing matters (e.g., gasses such as oxygen, and moisture) passes through a sheet member and deteriorates a medicinal substance, there are proposed a multi-chamber bag that employs a material capable of preventing penetration of adverse influence causing matters for the two sheet members of the bag body, and a multi-chamber bag that employs cover sheets, which can blocking an adverse influence causing matter, respectively attached to the two sheet members of the bag body so as to cover the medicinal-substance accommodation chamber.

In order to prevent penetration of adverse influence causing matters, sheet members and cover sheets employ, for example, block layers (e.g., aluminium layers formed by aluminium foils or by vapor deposition of aluminium) for blocking adverse influence causing matters, such as gasses or moisture, or have absorbent (e.g., calcium oxide or the like when an adverse influence causing matter is water) kneaded therein.

Whereby, it is possible to administer a medicinal substance, which is mixed with a medicinal solution (i.e., diluted medicinal substance, when the medicinal solution is a diluting solution) at the time of administration, while preventing deterioration of the medicinal substance within the medicinal-substance accommodation chamber until opening the bag.

Meanwhile, the multi-chamber bag having the above structure is preferably formed so that the condition of the medicinal substance within the bag can be checked to prevent erroneous administration of the medicinal substance. However, when an attempt is made to block penetration of adverse influence causing matters by employing the above structures, components enabling such function (e.g., calcium oxide as absorbent) may cause the sheet members or cover sheets to become milky white, or the presence of block layers (e.g., aluminium foils) may cause them to be opaque, which causes a problem of disabling checking the condition of the medicinal substance.

Accordingly, there is provided a multi-chamber bag, in which at least one of the sheet members is formed by a transparent sheet, and the cover sheets overlaid on the sheet members are separably attached so that they are separated away at the time of administration of the medicinal substance, thereby enabling checking the condition of the medicinal substance (cf. Patent Document 1, for example).

[Patent Document 1] JP-2005-28167A

DISCLOSURE OF THE INVENTION

Problems to be Solved by the Invention

However, removing the cover sheets is troublesome and therefore may hinder a prompt work when in emergency situation or an operation must be completed in a short time.

In consideration of the above circumstances, it is an object of the present invention to provide a multi-chamber bag that is capable of securely enabling checking a medicinal substance accommodated therein without the necessity to take a troublesome work, and securely preventing deterioration of a medicinal substance by blocking matters, which may deteriorate the medicinal substance, from reaching inside the medicinal-substance accommodation chamber.

Means for Solving Problems

According to the present invention, there is provided a multi-chamber bag that includes a bag body that has a strong seal part that joins two sheet members together to define an interior space of the bag body, and a weak seal part that partitions the interior space of the bag body into a medicinal-substance accommodation chamber and a medicinal-solution accommodation chamber. A pair of cover sheets are respectively overlaid on the two sheet members so as to cover the medicinal-substance accommodation chamber. The one sheet member and the one cover sheet overlaid on the one sheet member are formed by transparent sheets and the other cover sheet has a structure capable of absorbing adverse influence causing matters, which deteriorate a medicinal substance. Each of the cover sheets is joined to at least one of the facing sheet member and the opposite cover sheet protruding outward from the sheet members so as to form a first outside seal part that extends along the strong seal part defining the medicinal-substance accommodation chamber, and joined to the facing sheet member so as to form a second outside seal part that extends along the weak seal part defining the medicinal-substance accommodation chamber, thereby forming a space between the each of the cover sheet and the facing sheet member. An inside edge of at least a portion of the first outside seal part is located outward of an inside edge of the strong seal part defining the medicinal-substance accommodation chamber. A communication part for communication between a space on the side of the one cover sheet and a space on the side of the other cover sheet is formed in at least a portion between the inside edge of the strong seal part and the inside edge of the first outside seal part located outward of the inside edge of the strong seal part. Herein, the above-mentioned “structure capable of absorbing adverse influence causing matters” is intended to include a structure achieved by kneading a material for absorbing adverse influence causing matters, providing an absorption layer for absorbing adverse influence causing matters, or directly or indirectly providing absorbent for absorbing adverse influence causing matters to an inner surface of the cover sheet facing a corresponding sheet member.

With the multi-chamber bag having the above structure, the one sheet member and the one cover sheet are formed by transparent sheets, and therefore the inside of the medicinal-substance accommodation chamber can be directly and visually observed from this one side to check the condition of the medicinal substance accommodated therein.

Also, with the multi-chamber bag allowing the space formed on the side of the one cover sheet to be held in communication with the space on the side of the other cover sheet via the communication part, it is possible to allow adverse influence causing matters, which intruded into the space on the side of the one cover sheet through the one cover sheet, to flow into the space on the side of the other cover sheet via the communication part, and hence to be absorbed by the other cover sheet that has a structure capable of absorbing adverse influence causing matters. That is, since the space formed on the side of the one cover sheet is held in communication with the space formed on the side of the other cover sheet, the concentration of the intruded adverse influence causing matters tends to be evenly distributed through these two spaces. Therefore, as the adverse influence causing matters are subsequently absorbed by the other cover sheet, the concentration of the adverse influence causing matters within the both spaces is lowered. As a result, the adverse influence causing matters intruded through the one cover sheet are absorbed by the other cover sheet before passing the bag body (the sheet members). Also, the adverse influence causing matters, which are passing through the other cover sheet, are absorbed by the other cover sheet itself, so that they are unlikely to reach the interior space.

Whereby, the multi-chamber bag can block adverse influence causing matters from reaching the inside of the medicinal-substance accommodation chamber and hence prevent a medicinal substance accommodated therein from being deteriorated although absorbent or block layer, which may deteriorate the transparency of a sheet member, is not provided to a sheet member and a cover sheet on the one side of the multi-chamber bag.

According to a preferable embodiment of the present invention, the bag body has the medicinal-solution accommodation chamber arranged on one side of the medicinal-substance accommodation chamber, an unoccupied chamber arranged on another side of the medicinal-substance accommodation chamber, and a port member that is provided adjacent to the unoccupied chamber to be in communication therewith to discharge a medicinal substance mixed with a medicinal solution. The strong seal part includes a pair of first strong seal parts that join the opposite lateral ends of the sheet members together, and a pair of second strong seal parts that join the opposite transverse ends of the sheet members together. The weak seal part comprises two seal lines spaced apart from each other to partition the interior space into three compartments respectively serving as the medicinal-substance accommodation chamber, the medicinal-solution accommodation chamber and the unoccupied chamber. The cover sheets each have opposite lateral ends joined to at least the lateral side ends of the facing sheet members or the lateral side ends of the opposite cover sheet protruding outward from the sheet members. The communication part is formed between the inside edge of at least one of the first strong seal parts and the inside edge of the first outside seal part.

With the bag body having the unoccupied chamber therein, it is possible to prevent erroneous administration since a medicinal substance or a medicinal solution is not instantly discharged from the multi-chamber bag at the time of administration. Specifically, after the medicinal substance and the medicinal solution are first mixed together upon communication between the medicinal-substance accommodation chamber and the medicinal-solution accommodation chamber, the medicinal-substance accommodation chamber can be brought into communication with the unoccupied chamber. Thus, the medicinal substance is unlikely to be discharged before the mixing with the medical solution has not yet completed, and thus safety can be secured. Also, since the communicating portion is formed between the inside edge of any one of the first strong seal portions and the corresponding inside edge of the first outside seal portion, adverse influence causing matters, which have intruded into the space on the side of the one cover sheet, can be absorbed by the other cover sheet, enabling prevention of deterioration of a medicinal substance due to the adverse influence causing matters.

According to still another preferable embodiment of the present invention, the communication part is made up of two communication part members respectively formed between the inside edges of the pair of first strong seal parts defining the medicinal-substance accommodation chamber and the corresponding inside edges of the pair of first outside seal parts. With this arrangement having the two communication parts on the opposite sides of the bag body (sheet members), adverse influence causing matters intruded into the space on the side of the one cover sheet can be securely drawn into the space on the side of the other cover sheet to be absorbed.

According to yet another preferable embodiment of the present invention, the communication part is made up of an opening bored in the strong seal part. With this arrangement, it is possible to bring both the spaces into communication to each other via the opening while holding the medicinal-substance accommodation chamber under sealed condition. By the opening is meant a round hole, an elongated hole, a polygonal hole and the like.

According to still another preferable embodiment, the strong seal part is formed by joining the outer peripheral ends of the two sheet members together. The first outside seal part is formed by joining ends of the cover sheets protruding outward from the sheet members together. The communication part is formed by a gap that is defined between the outside edge of the strong seal part defining the medicinal-substance accommodation chamber and the inside edge of the first outside seal part. With this arrangement, it is possible to allow adverse influence causing matters, which has intruded into the space on the side of the one cover sheet, to be securely drawn into the space on the side of the other cover sheet via the communication part (gap) to be absorbed, even if an opening is not provided in the strong seal part.

Advantages of the Invention

As described above, according to the multi-chamber bag of the present invention, it is possible to securely check a medicinal substance accommodated therein without the necessity to perform a troublesome work, and block matters, which deteriorate the medicinal substance, from reaching the inside of the medicinal-substance accommodation chamber and hence securely prevent deterioration of the medicinal substance.

DESCRIPTION OF THE REFERENCE NUMERALS

Figures 1A, 1B:
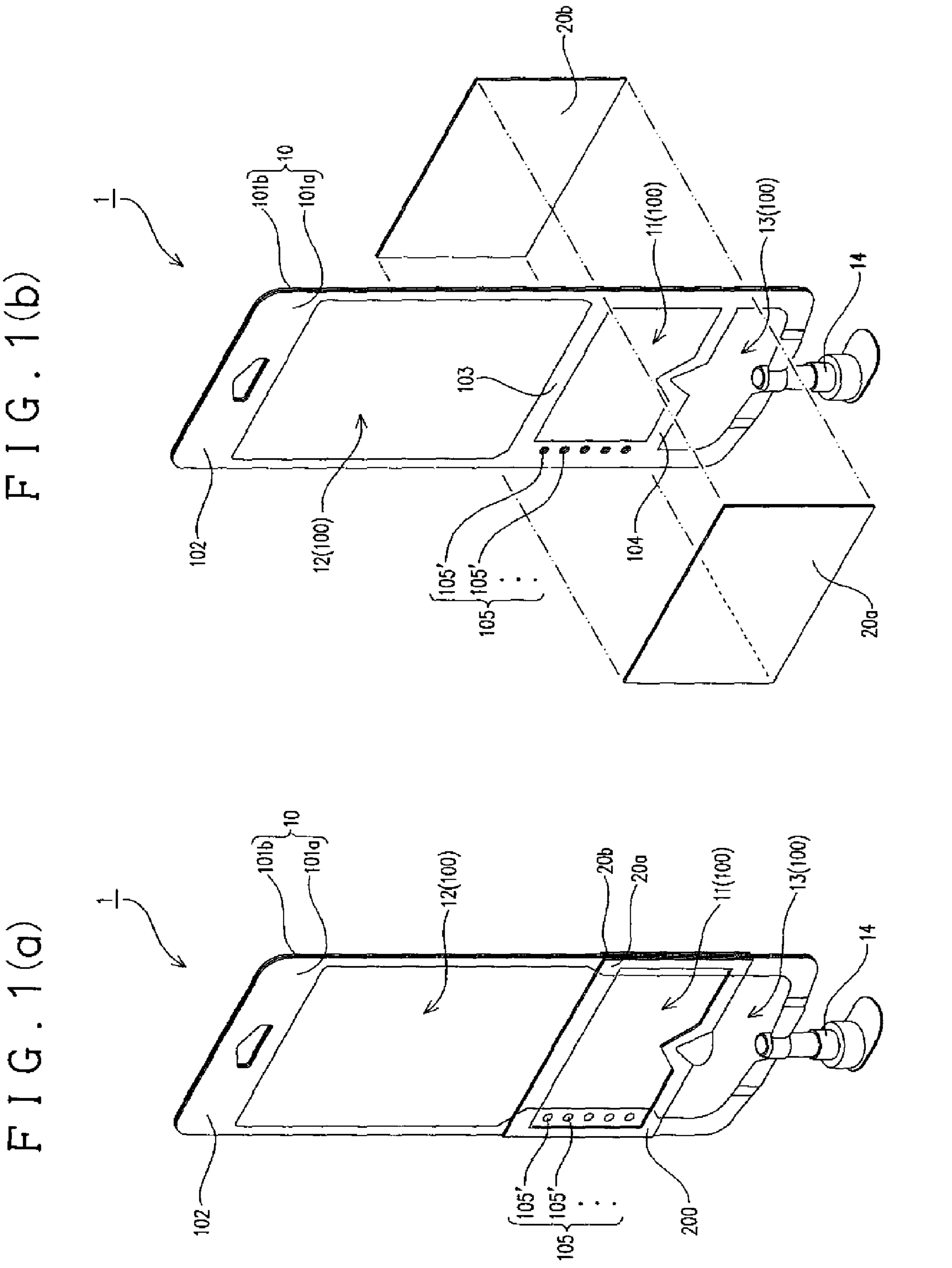
FIG. 1 are explanatory views of a multi-chamber bag according to a first embodiment of the present invention, in which FIG. 1(*a*) is an entire perspective view and FIG. 1(*b*) is an exploded perspective view.

1: multi-chamber bag, 10: bag body, 11: medicinal-substance accommodation chamber, 12: diluting-solution accommodation chamber (medicinal-solution accommodation chamber), 13: unoccupied chamber, 14: port member, 20*a*, 20*b*: cover sheets, 100: interior space, 101*a*, 101*b*: sheet members, 102: strong seal part, 102*a*, 102*b*: first strong seal parts, 102*c*, 102*d*: second strong seal parts, 103: fist weak seal part (weak seal part), 104: second weak seal part (weak seal part), 104*a*: easy-to-open part: 104*b*, 104*b*: straight parts, 105, 105": communication parts, 105': opening (round hole), 200: outside seal part, 200*c*, 200*d*: second outside seal parts, 200*a*, 200*b*: first outside seal parts, X: first space, Y: second space

DETAILED DESCRIPTION OF THE PREFERRED EMBODIMENT

Now, the description will be made for a multi-chamber bag of a first embodiment of the present invention with reference to the drawings attached hereto.

As illustrated in FIGS. 1 to 4, the multi-chamber includes a bag body 10 that has at least a medicinal-substance accommodation chamber 11 for accommodating powdered or liquid medicinal substance and a medicinal-solution accommodation chamber 12 for accommodating a medicinal solution, and a pair of cover sheets 20*a*, 20*b* that are provided on the opposite sides of the bag body 10 to cover the medicinal-substance accommodation chamber 11.

More specifically, a multi-chamber bag 1 of this embodiment includes the medicinal-substance accommodation chamber 11 for accommodating a medicinal substance, the medicinal-solution accommodation chamber 12 (hereinafter referred as a diluting-solution accommodation chamber) for accommodating a medicinal solution (a diluting solution), and an unoccupied chamber 13 that has a port member 14 provided adjacent to the unoccupied chamber 13 to be in communication therewith, which discharge a medicinal substance mixed and diluted with a diluting solution. From the view point of safeness in administering the medicinal substance, the medicinal-substance accommodation chamber 11 is located at an intermediate position with the medicinal-solution accommodation chamber 12 and the unoccupied chamber 13 provided on the opposite sides thereof, respectively. The multi-chamber bag 1 of this embodiment is designed to accommodate, as a medicinal substance, a powdered antibiotic that is deteriorated by moisture and oxygen in the medicinal-substance accommodation chamber 11, and, as a diluting solution (a medicinal solution), for example, a normal saline solution or a glucose solution in the medicinal-solution accommodation chamber 12. With the medicinal-solution accommodation chamber 12 held upward and the unoccupied chamber 13 held downward, the diluted medicinal substance, which has been prepared by mixing (diluting) the medicinal substance with the diluting solution, can be administered via the port member 14.

The bag body 10 is formed by two sheet members 101*a*, 101*b* overlapped and joined together. More specifically, the bag body 10 includes a strong seal part 102 that joins the two sheet members 101*a*, 101*b* together, thereby defining an interior space 100, and a weak seal part 103 that separably joins the sheet members 101*a*, 101*b* together, thereby partitioning the interior space 100 into the medicinal-substance accommodation chamber 11 and the medicinal-solution accommodation chamber 12.

The multi-chamber bag 1 of this embodiment includes the unoccupied chamber 13, and therefore the bag body 10 has two weak seal parts 103, 104 that separably join the two sheet members 101*a*, 101*b*, thereby partitioning the interior space 100 defined by the strong seal part 102 into three compartments. Whereby, the bag body 10 enables the medicinal-substance accommodation chamber 11 and the medicinal-solution accommodation chamber 12 to be brought into communication with each other by rupturing one weak seal part (hereinafter referred as a first weak seal part) 103, and enables the medicinal-substance accommodation chamber 11 and the unoccupied chamber 13 to be brought into communication with each other by rupturing the other weak seal part (hereinafter referred as a second weak seal part) 104.

In this embodiment, the two sheet members 101*a*, 101*b* have a substantially rectangular outer shape corresponding to the shape of the bag body 10 as viewed from the front side; the interior space 100 is defined by joining their outer peripheral ends together (thus forming the strong seal part 102); and the interior space 100 is partitioned into the medicinal-substance accommodation chamber 11, the medicinal-solution accommodation chamber 12 and the unoccupied chamber 13 by joining mutually facing portions of the sheet members 101*a*, 101*b* along different heights in the vertical direction (thus forming the first weak seal part 103 and the second weak seal part 104).

Figures 5A, 5B, 5C:
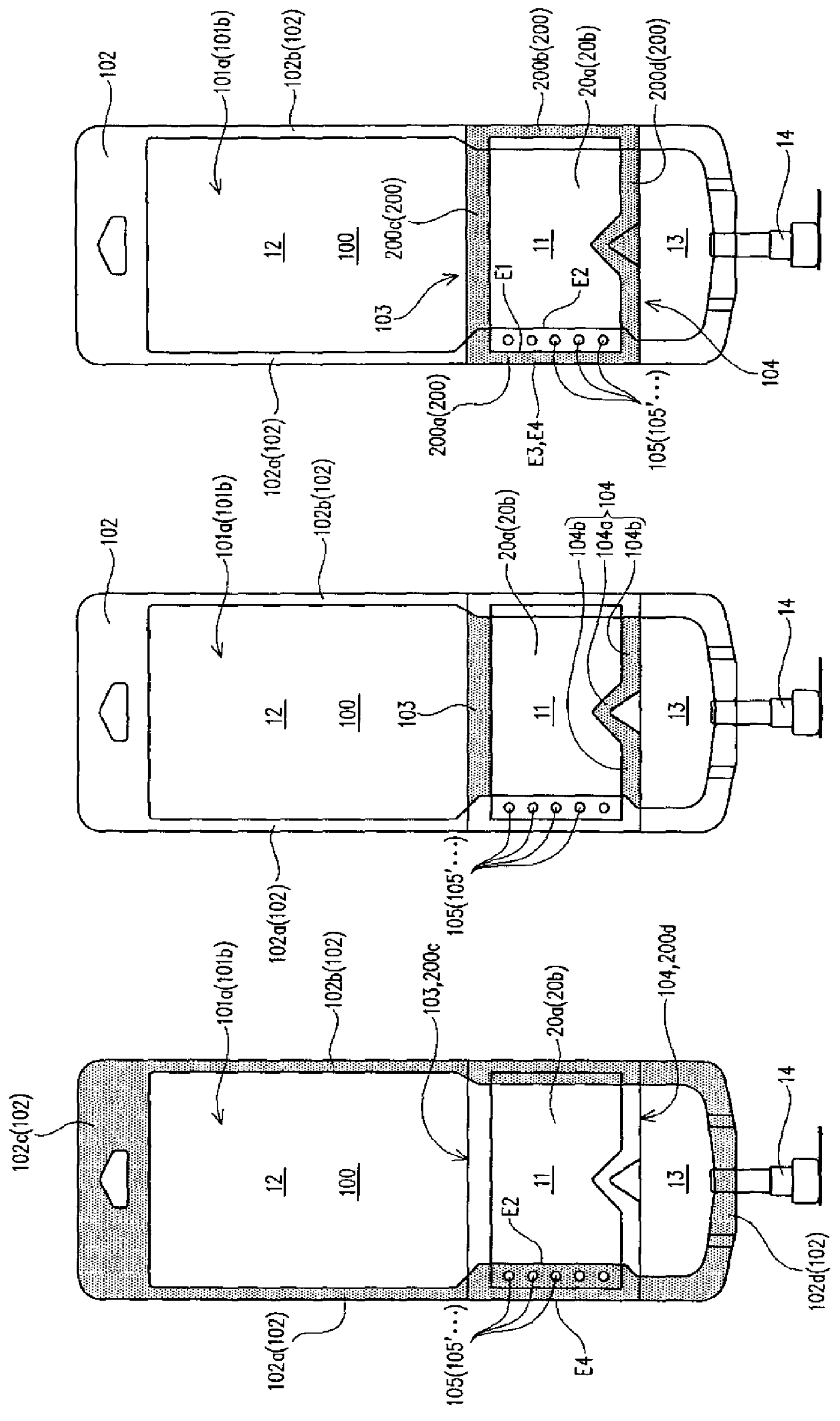
FIG. 5 are explanatory views of the multi-chamber bag of the first embodiment, in which FIG. 5(*a*) is a front view with a strong seal part joining the sheet members together being exaggerated, FIG. 5(*b*) is a front view with weak seal parts (a first weal seal part and a second weak seal part) separably joining the sheet members together being exaggerated, and FIG. 5(*c*) is a front view with an outside seal part joining a cover sheet to a bag body being exaggerated.

As illustrated in FIG. 5(*a*), the strong seal part 102 includes a pair of first strong seal parts 102*a*, 102*b* formed along the opposite lateral ends with a space therebetween, thereby defining the interior space 100, and a pair of second strong seal parts 102*c*, 102*d* formed to join together the opposite ends of the pair of first strong seal parts 102*a*, 102*b*. In this embodiment, the outer peripheral ends of the rectangular sheet members 101*a*, 101*b* are joined together, thereby forming the strong seal part 102, and therefore the first strong seal parts 102*a*, 102*b* and the pair of second strong seal parts 102*c*, 102*d* together define a substantially rectangular shape of the interior space 100 as viewed from the front side.

Portions of the pair of first strong seal parts 102*a*, 102*b*, which define the medicinal-substance accommodation chamber 11 and the unoccupied chamber 13, are wider than the portions thereof defining the medicinal-solution accommodation chamber 12. Portions of the one first strong seal parts 102*a* defining the medicinal-substance accommodation chamber 11 are wider than portions thereof defining the unoccupied chamber 13.

Then, the wider portion of the one first strong seal part 102*a*, which defines the medicinal-substance accommodation chamber 11, has a communication part 105 for communication between a fist space X and a second space Y hereinafter described (cf. FIG. 2(*c*)). The communication part 105 of this embodiment is made up of plural openings 105' . . . located away from each other in a direction in which the one first strong seal part 102*a* extends. The openings 105' each are formed by a round hole. The opening area of the communication part 105 is preferably set to be 1% to 20% of an unsealed portion (hereinafter referred as a cover area) surrounded by portions (hereinafter described first outer seal parts 200*a*, 200*b*, and second outer seal parts 200*c*, 200*d*, (see FIG. 5(*c*))) through which the outer peripheral ends of the cover sheets 20*a*, 20*b* are sealed respectively to the sheet members 101*a*, 101*b*. That is, when the opening area is less than 1% of the cover area, the passing efficiency of adverse influence causing matters (the absorption efficiency of adverse influence causing matters by the cover sheet 20*b*) is lowered, and when the opening area is greater than 20%, the width of the one first strong seal part 102*a*, in which the communication part 105 (openings 105') is to be provided, must be widen, which causes a medicinal substance accommodation space of the medicinal-substance accommodation chamber 11 to be decreased, and may hinder opening of the weak seal parts 103, 104. Thus, the opening area is preferably set to be 1% to 20% of the cover area.

As illustrated in FIG. 5(*b*), the first weak seal part 103 has the opposite ends connected to the strong seal parts 102 (a pair of the first strong seal parts 102*a*, 102*b* located along the opposite lateral ends of the bag body 10), which are spaced apart from each other to define the interior space 100, and is formed by a straightforward band-like portion in this embodiment. On the contrary, the second weak seal part 104 is located away from and parallel to the first weak part 103, and has the opposite ends connected to the strong seal part 102 (a pair of the first strong seal parts 102*a*, 102*b*), which define the interior space 100, in the same manner as the first weak seal part 103.

The second weak seal part 104 of this embodiment is made up of an easy-to-open part 104*a* formed to project towards the medicinal-substance accommodation chamber 11 and a pair of straight parts 104*b*, 104*b* extending straight from the opposite ends of the easy-to-open part 104*a* and connected to the strong seal part. The easy-to-open part 104*a* is formed by an angular zone with its apex located close to the medicinal-substance accommodation chamber 11, and more specifically, has edges respectively located offset from the medicinal-substance accommodation chamber 11 and the unoccupied chamber 13, in which the apexes of these edges are located close to the medicinal-substance accommodation chamber 11. In this easy-to-open part 104*a*, the apex of the edge close to the unoccupied chamber 13 is located closer to the medicinal-substance accommodation chamber 11 than the edge of the straight parts 104*b*, 104*b* close to the medicinal-substance accommodation chamber 11 is. Whereby, the second weak seal part 104 can be ruptured first at the easy-to-open part 104*a* when an inner pressure is being applied by pressing the bag body 10.

Figures 2A, 2B, 2C:
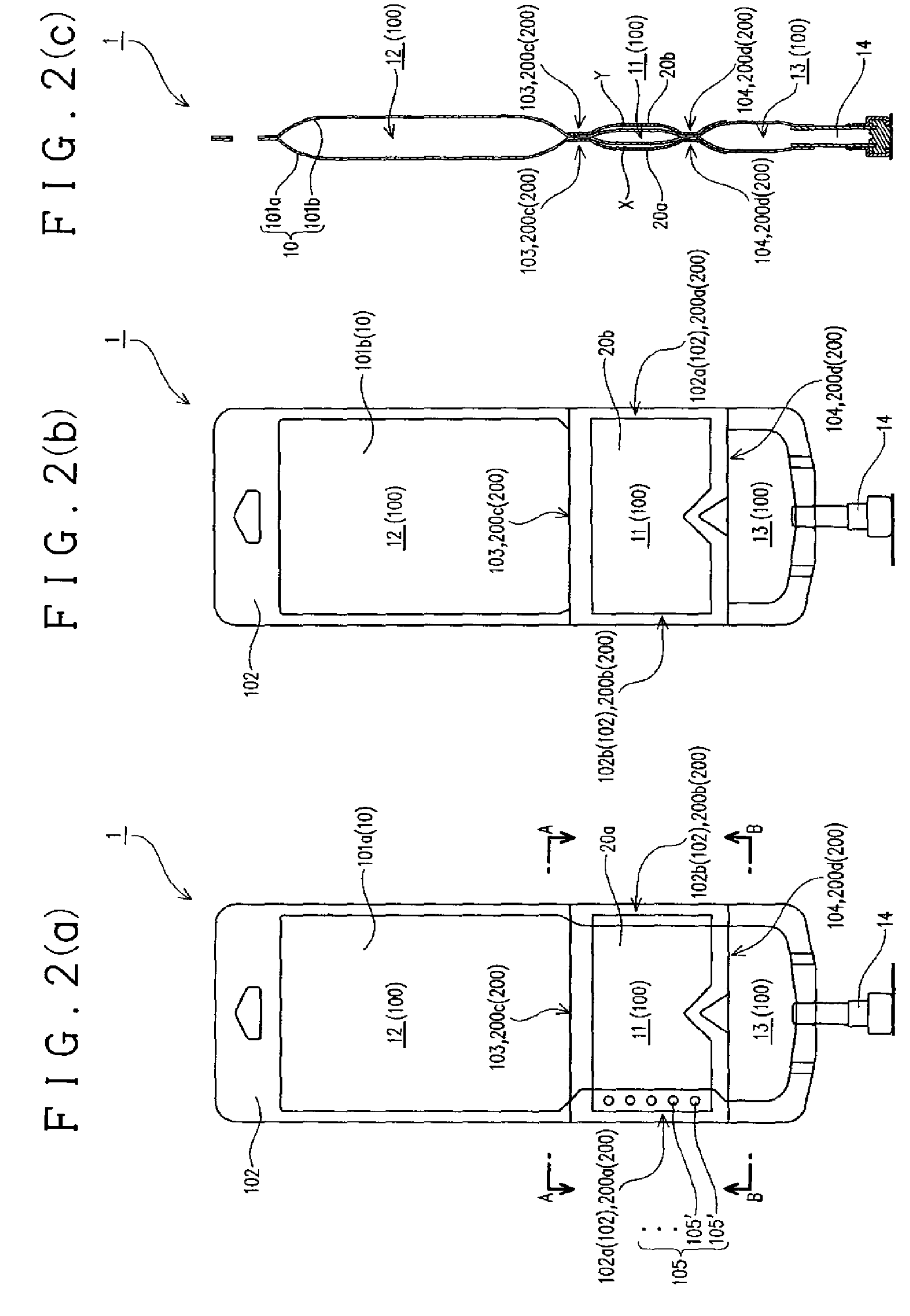
FIG. 2 are explanatory views of the multi-chamber bag of the first embodiment, in which FIG. 2(*a*) is a front view with a medicinal substance and a diluting solution chamber omitted, FIG. 2(*b*) is a rear view with a medicinal substance and a diluting solution chamber omitted, and FIG. 2(*c*) is a cross sectional view taken along a vertical axis.
Figure 3A:
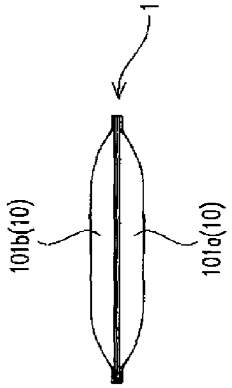
FIG. 3 are explanatory views of the multi-chamber bag of the first embodiment, in which FIG. 3(*a*) is a plan view, FIG. 3(*b*) is a bottom view and FIG. 3(*c*) is a side view.
Figure 3B:
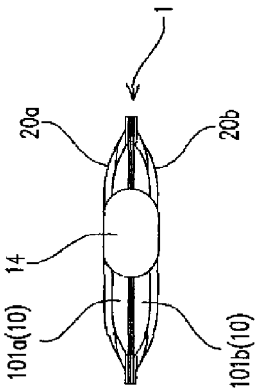
Figure 3C:
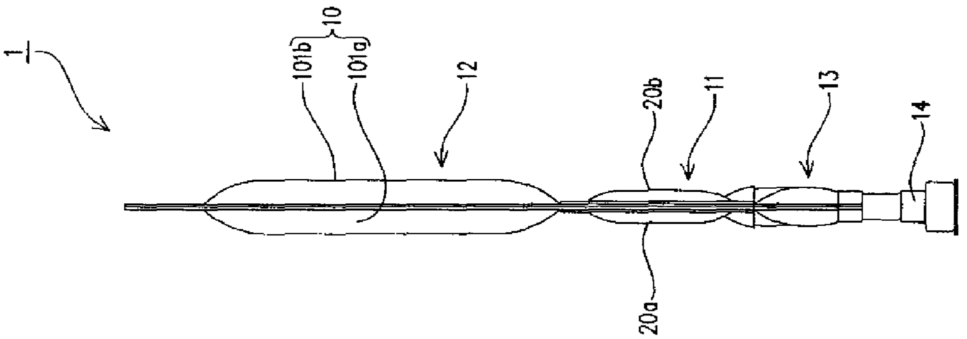
Figure 4:
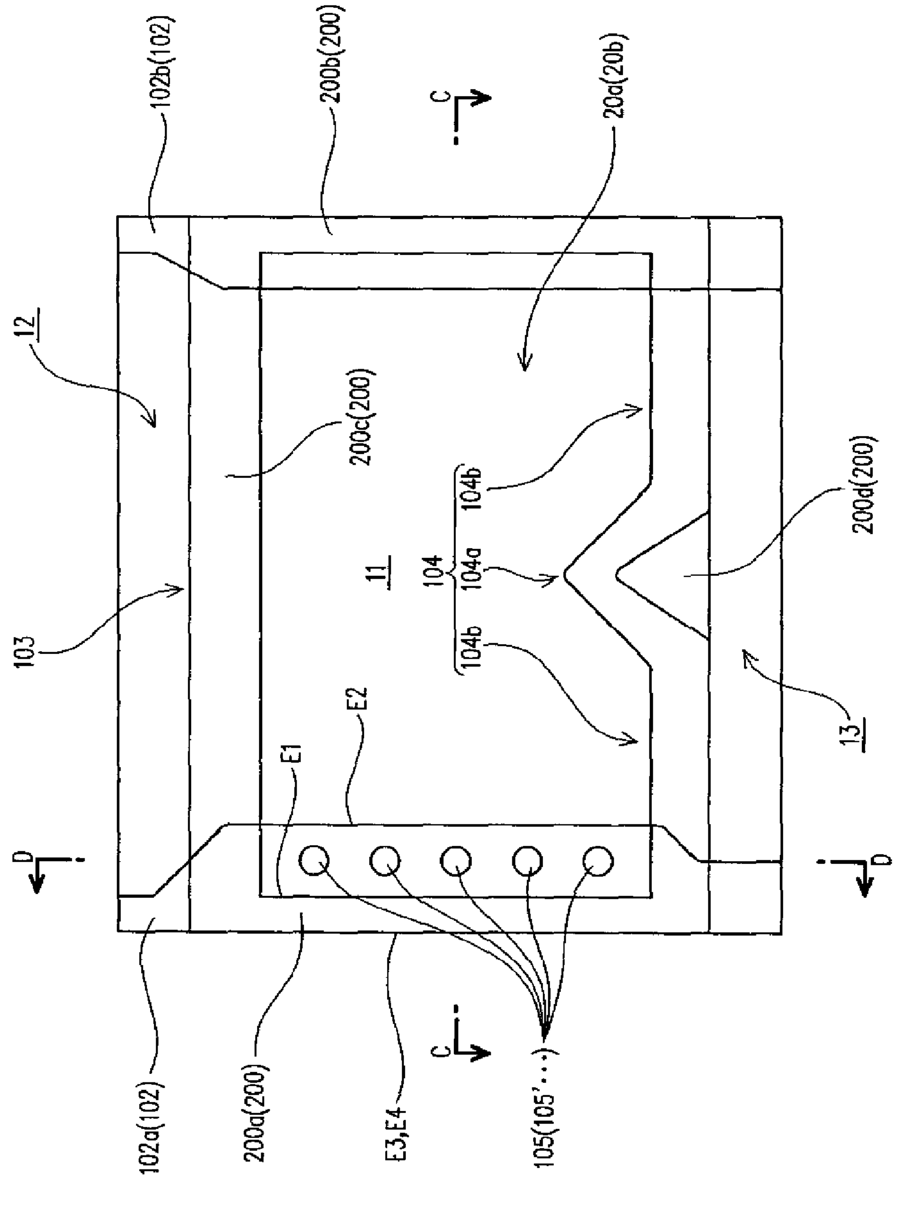
FIG. 4 is a partially enlarged view of a portion A-B in FIG. 2(*a*) of the multi-chamber bag of the first embodiment.

Then, as illustrated in FIG. 2(*c*), the port member 14 is held between the two sheet members 101*a*, 101*b* of the bag body 10 and joined thereto so as to bring the unoccupied chamber 13 into communication with the inside of the port member 14.

The two sheet members 101*a*, 101*b* of the bag body 10 each have a single layer structure or a plural layer structure, and at least the one sheet member 101*a*, which becomes the front side of the bag body 10, employs a transparent sheet. As this transparent sheet, it is preferable to employ a singular layer or multi-layers of various resins known as those for medical containers, such as low-density polyethylene, medium-density polyethylene, high-density polyethylene, polypropylene, polyamide, polyimide, ethylenevinyl alcohol copolymer, polyvinyl alcohol (PVA), polyethylene terephthalate, cycloolefin copolymer, and cycloolefin polymer. Especially, for the two sheet members (transparent sheets) 101*a*, 101*b*, it is preferable to employ a multi-layer structure made up of a mixed resin layer (thickness: 20 μm) of polyethylene (PE) and polypropylene (PP), a polyethylene (PE) layer (thickness: 60 μm), a cycloolefin polymer (COC) layer or a cycloolefin polymer (COP) layer (thickness: 20 μm), and a polyethylene (PE) layer (thickness: 50 μm).

In the multi-chamber bag 1 of this embodiment, the joining of the sheet members 101*a*, 101*b*, the joining of the sheet members 101*a*, 101*b* to the cover sheets 20*a*, 20*b*, the joining of the port member 14 to the sheet members 101*a*, 101*b* are achieved by heat adhesion.

As illustrated in FIG. 5(*c*), the pair of cover sheets 20*a*, 20*b* each have opposite transverse ends and opposite lateral ends respectively joined to the sheet members 101*a*, 101*b*, and thus these joined portions constitute an outside seal part 200 that surrounds the medicinal-substance accommodation chamber 11.

In this embodiment, as illustrated in FIGS. 1 and 2, the cover sheets 20*a*, 20*b* each have a size and a substantially square shape corresponding to the shape of the medicinal-substance accommodation chamber 11 of the bag body 10. Specifically, the cover sheets 20*a*, 20*b* each are substantially identical in shape and size to the area defined by the outside edges of the pair of first strong seal parts 102*a*, 102*b* defining the medicinal-substance accommodation chamber 11, the first weak seal part 103 and the second weak seal part 104 (straight parts 104*b*, 104*b*).

The multi-chamber bag 1 of this embodiment is designed to accommodate an antibiotic, which is deteriorated by moisture and oxygen in the medicinal-substance accommodation chamber 11, and therefore the pair of cover sheets 20*a*, 20*b* are imparted with a moisture barrier property and an oxygen barrier property so as to block moisture and oxygen from passing therethrough. The cover sheets 20*a*, 20*b* preferably have a moisture penetration rate of 5 $g/m^2 \cdot 24$ hrs. or lower, and an oxygen penetration rate of 1 $cc/m^2 \cdot day \cdot atm$ or lower.

Figure 6A:
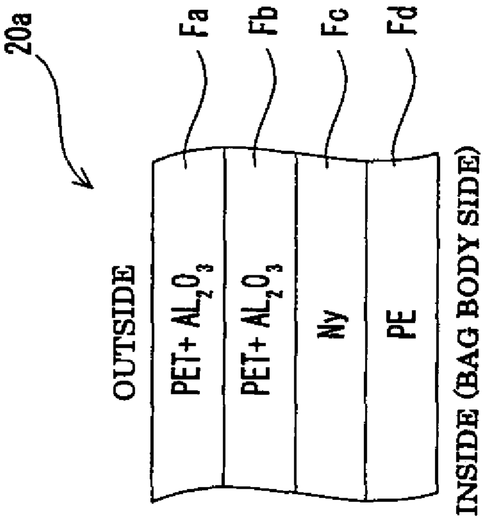
FIG. 6 are explanatory views for explaining layer structures of a cover sheet of the multi-chamber bag of the first embodiment, in which FIG. 6(*a*) illustrates a layer structure of one cover sheet provided on the front side, and FIG. 6(*b*) illustrates a layer structure of another cover sheet provided on the rear side.
Figure 6B:
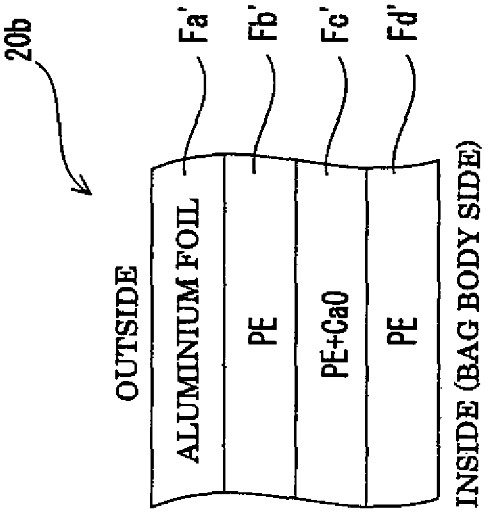

For the one cover sheet 20*a*, a sheet that is still transparent while having a moisture barrier property and an oxygen barrier property is employed, as mentioned above. As this transparent sheet, it is possible to employ a sheet in which aluminium oxide (alumina) and/or silicon oxide (silica) are vapor deposited over polyethylene terephthalate (PET) or polyamide, or various known resin sheets, such as polyvinylidene chloride. A sheet may be formed by laminating a resin having a moisture barrier property to a resin having an oxygen barrier property. Examples of the resin having an oxygen barrier property include polyvinyl alcohol (PVA) and ethylenevinyl alcohol copolymer (EVOH) in addition to the above. In this embodiment, as illustrated in FIG. 6(*a*), the one cover sheet 20*a* employs a four layer structure that has a first layer Fa and a second layer Fb on the outer side, in which alumina ($Al_2O_3$) is deposited over polyethylene terephthalate (PET), and a third layer Fc formed of Nylon (Ny) and a fourth layer Fd formed of polyethylene (PE) laminated together in this order on the inner side.

On the other hand, for the other cover sheet 20*b*, a sheet that has a moisture absorption property, as well as a moisture barrier property and an oxygen barrier property is employed. As this sheet, it is possible to employ a sheet that has aluminium foil, polyethylene terephthalate (PET) or polyamide vapor deposited with aluminium, and a moisture absorption layer laminated thereto. In this embodiment, as illustrated in FIG. 6(*b*), the other cover sheet 20*b* employs a four layer structure that has a first layer Fa' formed of aluminium foil, a second layer Fb' formed of polyethylene (PE), a third layer Fc' formed by kneading calcium oxide (CaO) as a moisture absorbent into polyethylene (PE), and a fourth layer Fd' formed of polyethylene (PE) laminated in this order from the outer side. Since the other cover sheet 20*b* has a layer of aluminium foil or a layer deposited with aluminium, it has a higher moisture barrier property and a higher oxygen barrier property than the one cover sheet 20*a* formed by a transparent sheet, as well as has a light blocking effect, which is effective in preventing deterioration of a medicinal substance, although it is opaque.

As illustrated in FIG. 2(*a*), the one cover sheet 20*a* is overlaid onto the one sheet member 101*a* so as to cover the medicinal-substance accommodation chamber 11, and the other cover sheet 20*b* is overlaid onto the other sheet member 101*b* so as to cover the medicinal-substance accommodation chamber 11. As illustrated in FIG. 5(*c*), the outside seal part 200, which is formed by joining the cover sheets 20*a*, 20*b* to the sheet members 101*a*, 101*b*, includes a pair of first outside seal parts 200*a*, 200*b* along the pair of first strong seal parts 102*a*, 102*b*, and a pair of second outside seal parts 200*c*, 200*d* along the first weak seal part 103 and the second weak seal part 104. The pair of second outside seal parts 200*c*, 200*d* are formed to be substantially entirely overlapped to the first weak seal part 103 and the second weak seal part 104. On the other hand, the one first outside seal part 200*a* on one side (one lateral end) of the pair of first outside seal parts 200*a*,

200*b* has an inside edge E1 located outward of an inside edge E2 of the strong seal part 102 (the one first strong seal part 102*a*) defining the medicinal-substance accommodation chamber 11. In this embodiment, the first outside seal part 200*a* has a width narrower than the one first strong seal part 102*a* and is formed to be overlapped to the one first strong seal part 102*a*. The other first outside seal part 200*b* may have a width corresponding to the first strong seal part 102*b*, but is formed with a width corresponding to the one first outside seal part 200*a* in this embodiment.

Since the cover sheets 20*a*, 20*b* of this embodiment are formed with a size and a shape corresponding to the area defined by the outside edges of the pair of first strong seal parts 102*a*, 102*b*, the first weak seal part 103 and the second weak seal part 104, the first outside seal parts 200*a*, 200*b* have an outside edge E3 aligned with the outside edges E4 of the first strong seal parts 102*a*, 102*b* (the lateral ends of the sheet members 101*a*, 101*b*). Whereby, as described above, the first outside seal part 200*a* has a width narrower than the first strong seal part 102 so that the one first outside seal parts 200*a*, 200*b* are formed so as to detour around the communication part 105 formed in the first strong seal part 102.

Figure 7A:
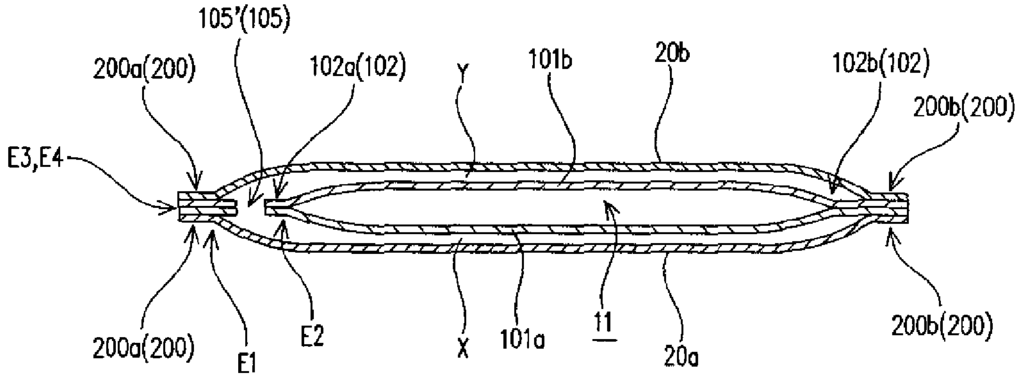
FIG. 7 are cross sectional views of a portion of the multi-chamber bag of the first embodiment, in which FIG. 7(*a*) is a cross sectional view taken along a line C-C in FIG. 4, and FIG. 7(*b*) is a cross sectional view taken along a line D-D in FIG. 4.
Figure 7B:
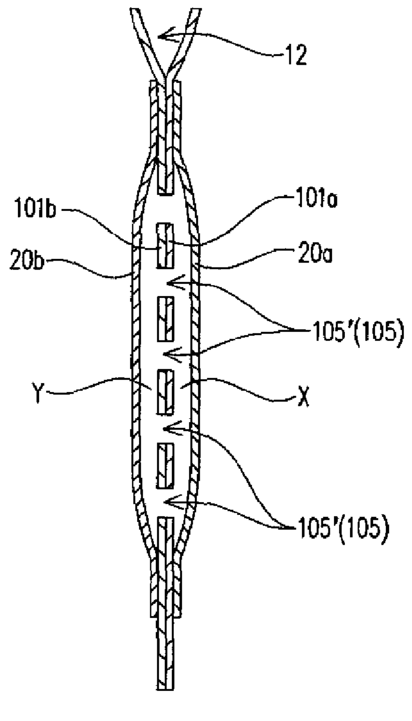

By joining the pair of cover sheets 20*a*, 20*b* to the bag body 10 (the sheet members 101*a*, 101*b*), a space (hereinafter referred as a fist space) X is formed between the one sheet member 101*a* (the bag body 10) and the one cover sheet 20*a*, and a space (hereinafter referred as a second space) Y is formed between the other sheet member 101*b* (the bag body 10) and the other cover sheet 20*b*, as illustrated in FIGS. 2(*c*) and 7(*a*). The first space X and the second space Y are held in communication with each other via the communication part 105 (the holes 105', . . . ) provided between the inside edge E1 of the outside seal part 200 (the one first outside seal part 200*a*) on one lateral side of the cover sheets 20*a*, 20*b* and the inside edge E2 of the strong seal part 102 (the one first strong seal part 102*a*) on one lateral side of the bag body 10, as illustrated in FIGS. 7(*a*) and 7(*b*).

Now, the description will be made for the function of the multi-chamber bag 1 of this embodiment having the above structure. Although the one cover sheet 20*a* of the multi-chamber bag 1 has a moisture barrier property and an oxygen barrier property, the moisture barrier property is not satisfactory since the transparency must be secured, and a moisture absorption capacity is not imparted. Thus, moisture passes through the one cover sheet 20*a* and reaches the inside of the first space X. However, in the multi-chamber bag 1 of this embodiment, the other cover sheet 20*b* is imparted with a higher moisture barrier property and a higher oxygen barrier property than the one cover sheet 20*a* and is further imparted with a moisture absorption capacity, and the first space X is held in communication via the communication part 105 with the second space Y formed between the other cover sheet 20*b* and the bag body 10, so that moisture intruded into the first space X is intruded into the second space Y via the communication part 105. Accordingly, moisture intruded into the second space Y is absorbed by the moisture absorption capacity of the other cover sheet 20*b*. More specifically, when the other cover sheet 20*b* absorbs moisture, the moisture concentration tends to be evenly distributed by the first space X and the second space Y communicated to each other. As a result, moisture intruded into the first space X is drawn into the second space Y and hence absorbed by the other cover sheet 20*b*. Whereby, oxygen and moisture are unlikely to reach the inside of the medicinal-substance accommodation chamber 11, and hence the medicinal substance accommodated therein is prevented from being deteriorated.

Figure 8B:
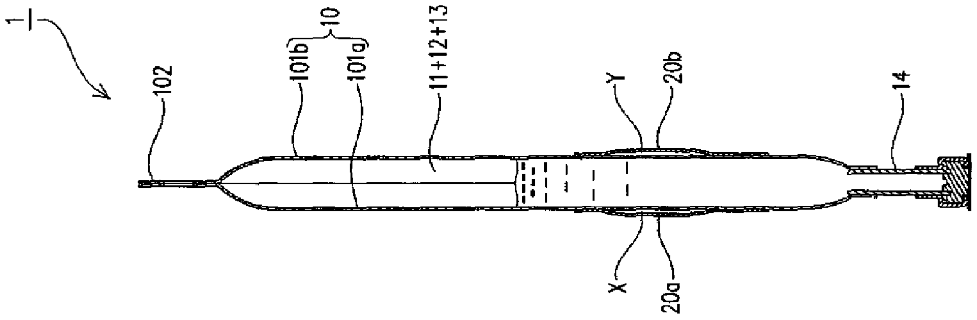
FIG. 8 are explanatory views of the multi-chamber bag of the first embodiment, in which FIG. 8(*a*) is a front view illustrating the bag with a medicinal substance and a diluting solution accommodated therein, and FIG. 8(*b*) is a cross sectional view taken along a vertical axis of the bag with weak seal parts (a first weak seal part and a second weak seal part) ruptured and hence the respective chambers held in communication with each other.
Figure 8A:
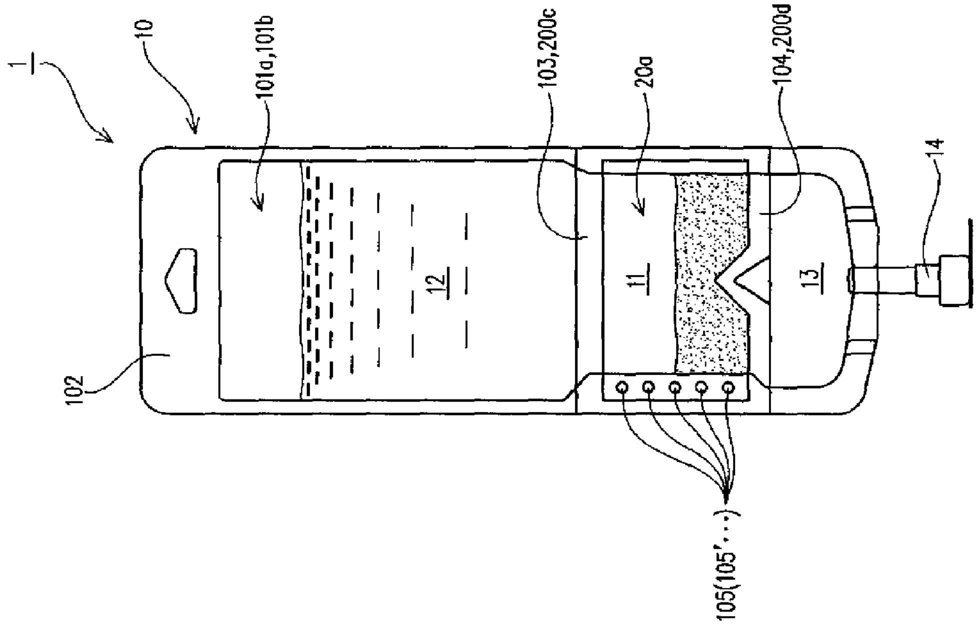
Figure 9A:
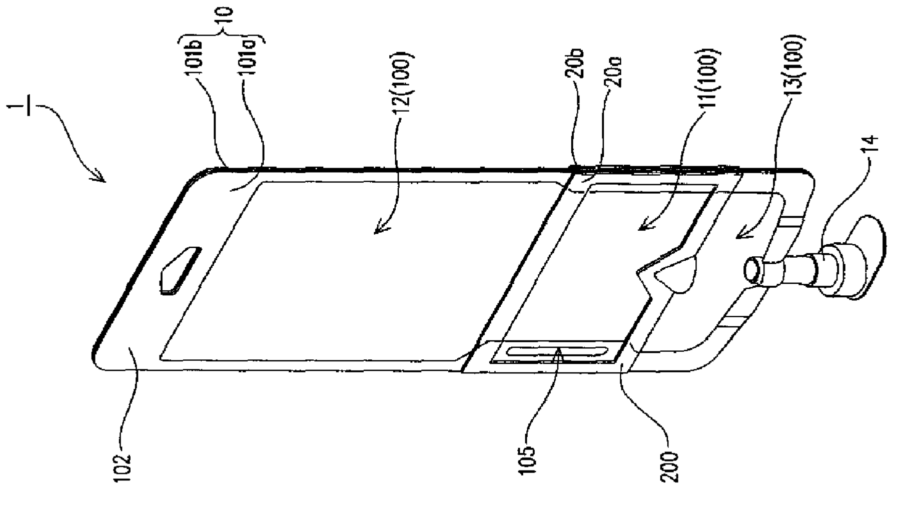
FIG. 9 are explanatory views of the multi-chamber bag of a second embodiment of the present invention, in which FIG. 9(*a*) is an entire perspective view, and FIG. 9(*b*) is an exploded perspective view.
Figure 9B:
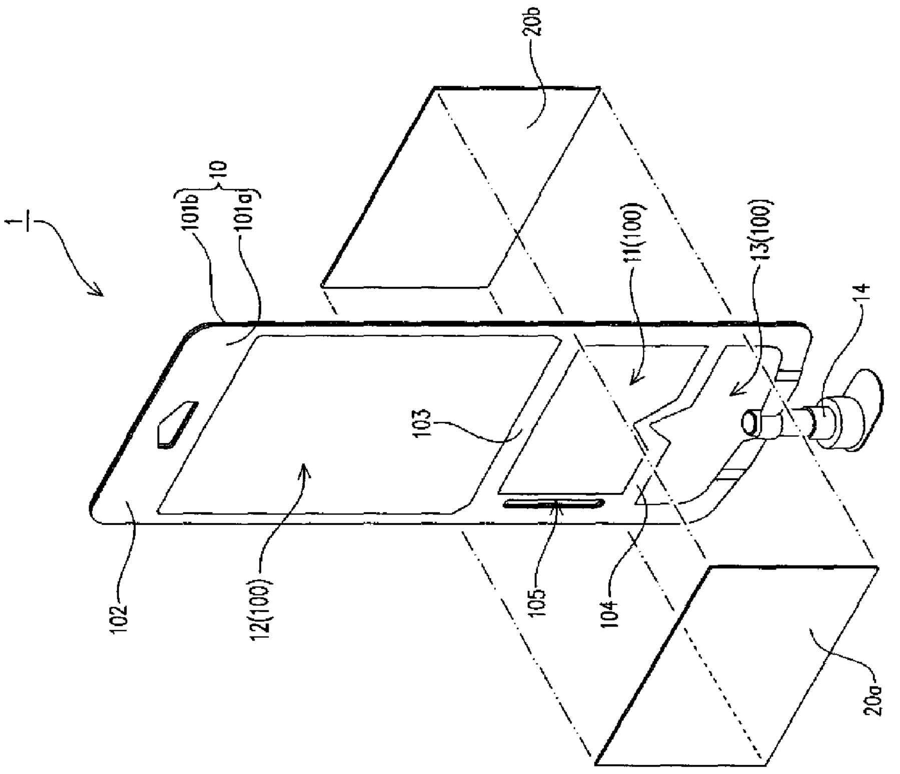
Figures 10A, 10B, 10C:
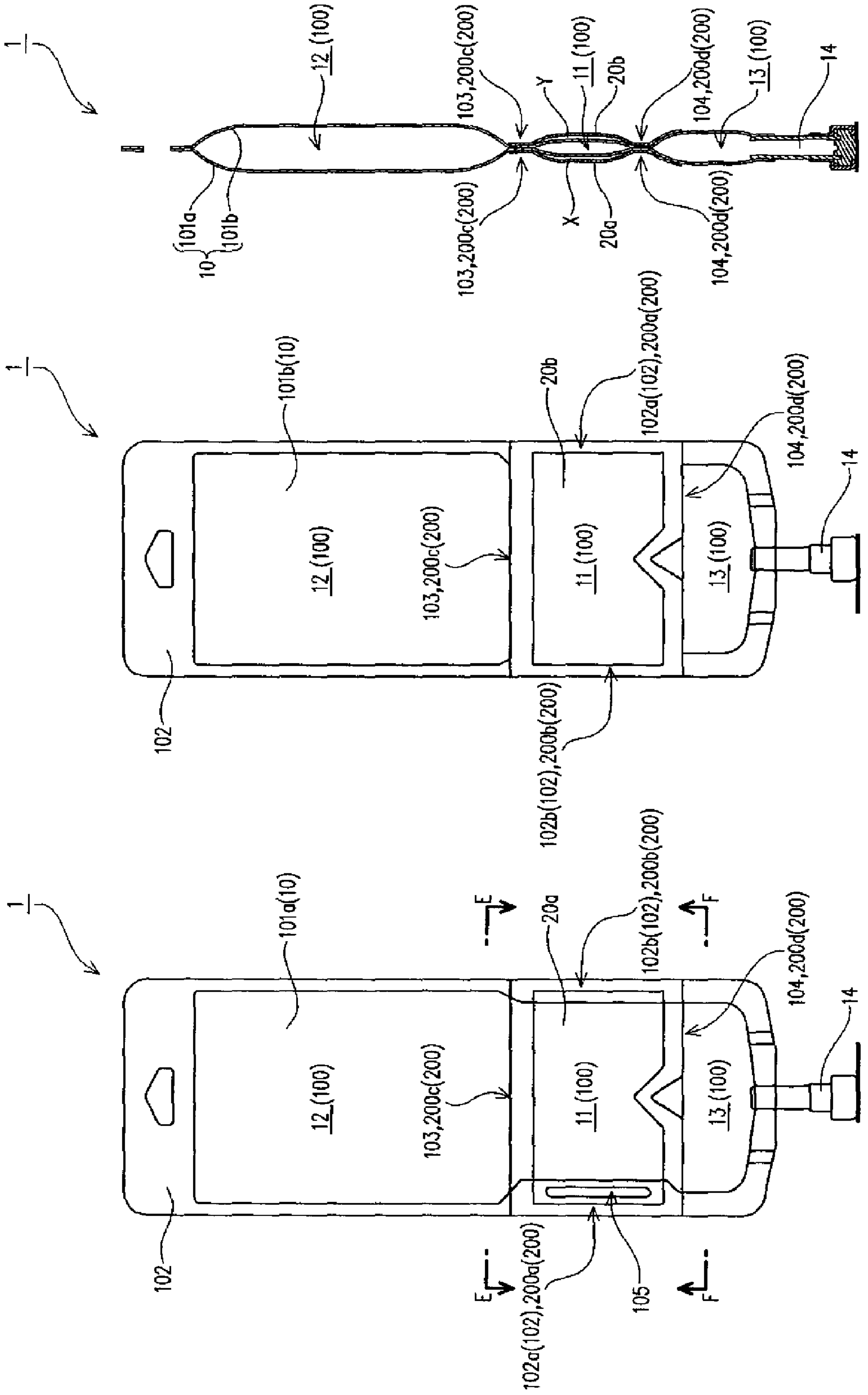
FIG. 10 are explanatory views of the multi-chamber bag of the second embodiment, in which FIG. 10(*a*) is a front view with a medicinal substance and a diluting solution chamber omitted, FIG. 10(*b*) is a rear view with a medicinal substance and a diluting solution chamber omitted, and FIG. 10(*c*) is a cross sectional view taken along a vertical axis of the bag.
Figure 11A:
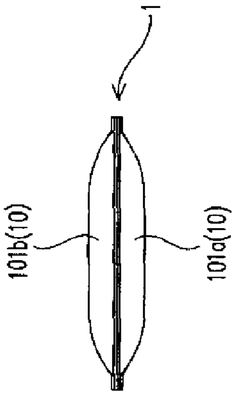
FIG. 11 are explanatory views of the multi-chamber bag of the second embodiment, in which FIG. 11(*a*) is a plan view, FIG. 11(*b*) is a bottom view and FIG. 11(*c*) is a side view.
Figure 11B:
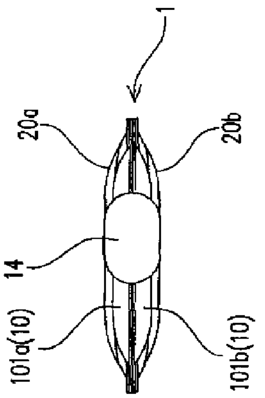
Figure 11C:
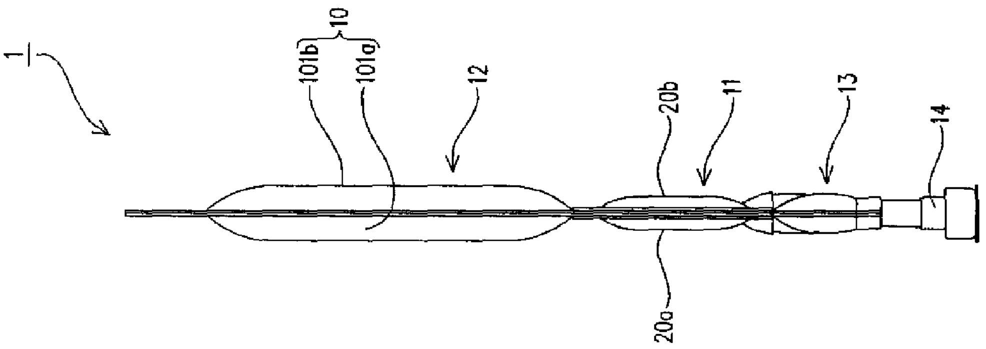
Figure 12:
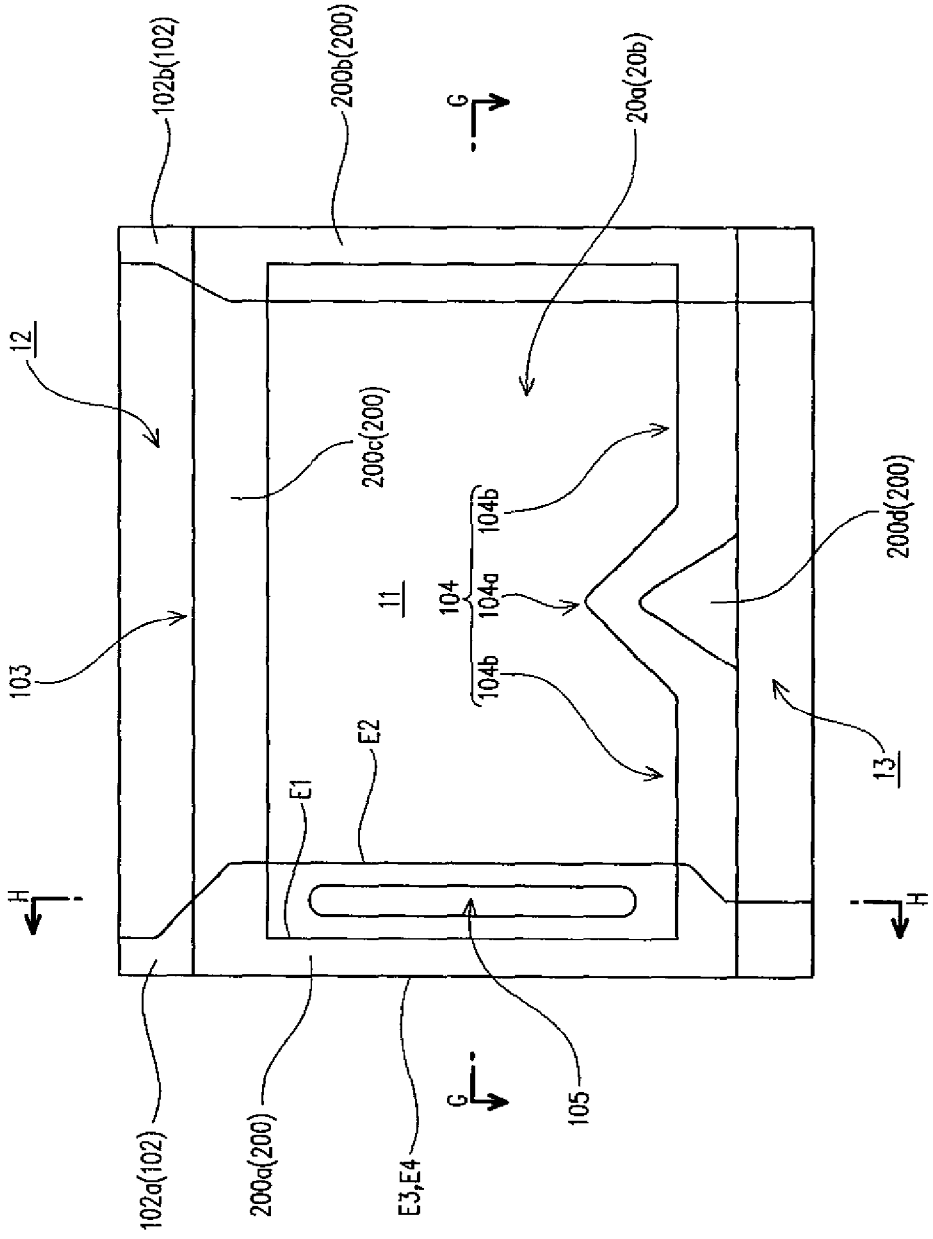
FIG. 12 is a partially enlarged view of a portion E-F in FIG. 10(*a*) of the multi-chamber bag of the second embodiment.

Since the one cover sheet 20*a* and the bag body 10 (the one sheet member 101*a*) are transparent, a medicinal substance accommodated in the medicinal-substance accommodation chamber 11 can be visually observed, as illustrated in FIG. 8(*a*), and when the medicinal-substance accommodation chamber 11 and the diluting-solution accommodation chamber 12 are communicated with each other by rupturing the first weak part 103, the diluted condition of the medicinal substance can be checked, as illustrated in FIG. 8(*b*). Then, by rupturing the second weak seal part 104, the diluted medicinal substance can be administered via the unoccupied chamber 13 and the port member 14.

As described above, in the multi-chamber bag 1 of this embodiment, the one sheet member 101*a* and the one cover sheet 20*a* are formed by transparent sheets, and therefore it is possible to securely check the conditions of the medicinal substance at a glance without the necessity to perform a troublesome work, such as peeling of the cover sheet 20*a*. Also, the communication part 105 for communication between the first space X formed between the one sheet member 101*a* and the one cover sheet 20*a* and the second space Y formed between the other sheet member 101*b* and the other cover sheet 20*b* is formed between the inside edge E1 of the outer seal part 200 on at least one lateral side of the cover sheets 20*a*, 20*b* and the inside edge E2 of the strong seal part 102 on at least one lateral side of the bag body 10. With this arrangement, moisture, which has passed through the one cover sheet 20*a* and intruded into the first space X, flows into the second space Y and thus can be absorbed by the other cover sheet 20*b* defining the second space Y.

Since the pair of cover sheets 20*a*, 20*b* are imparted with an oxygen barrier property, oxygen that deteriorates an antibiotic is unlikely to pass therethrough, and thereby the antibiotic can also be prevented from being deteriorated. The multi-chamber bag 1 of this embodiment is imparted with a light blocking effect by providing the first layer Fa' formed of aluminium foil to the other cover sheet 20*b*. With this arrangement, when the multi-chamber bag 1 is folded into two with the other cover sheet 20*b* facing outward, light does not directly hit the medicinal-substance accommodation chamber 11 and hence it is possible to prevent deterioration of the antibiotic due to the irradiation of light.

The communication part 105 is formed of plural holes 105' . . . bored in the strong seal part 102, and therefore the first space X and the second space Y can be communicated with each other via the respective holes 105' . . . while holding the medicinal-substance accommodation chamber 11 under sealed condition.

Now, the description will be made for the multi-chamber bag of a second embodiment of the present invention. The multi-chamber bag of this embodiment is the same as the multi-chamber bag of the first embodiment except that the communication part for communication between the first space and the second space has a different shape. Accordingly, the identical or corresponding elements to those of the first embodiment will be given the same names and the same reference codes to omit the description thereof, and the description will be made only for the different elements.

Figures 13A, 13B, 13C:
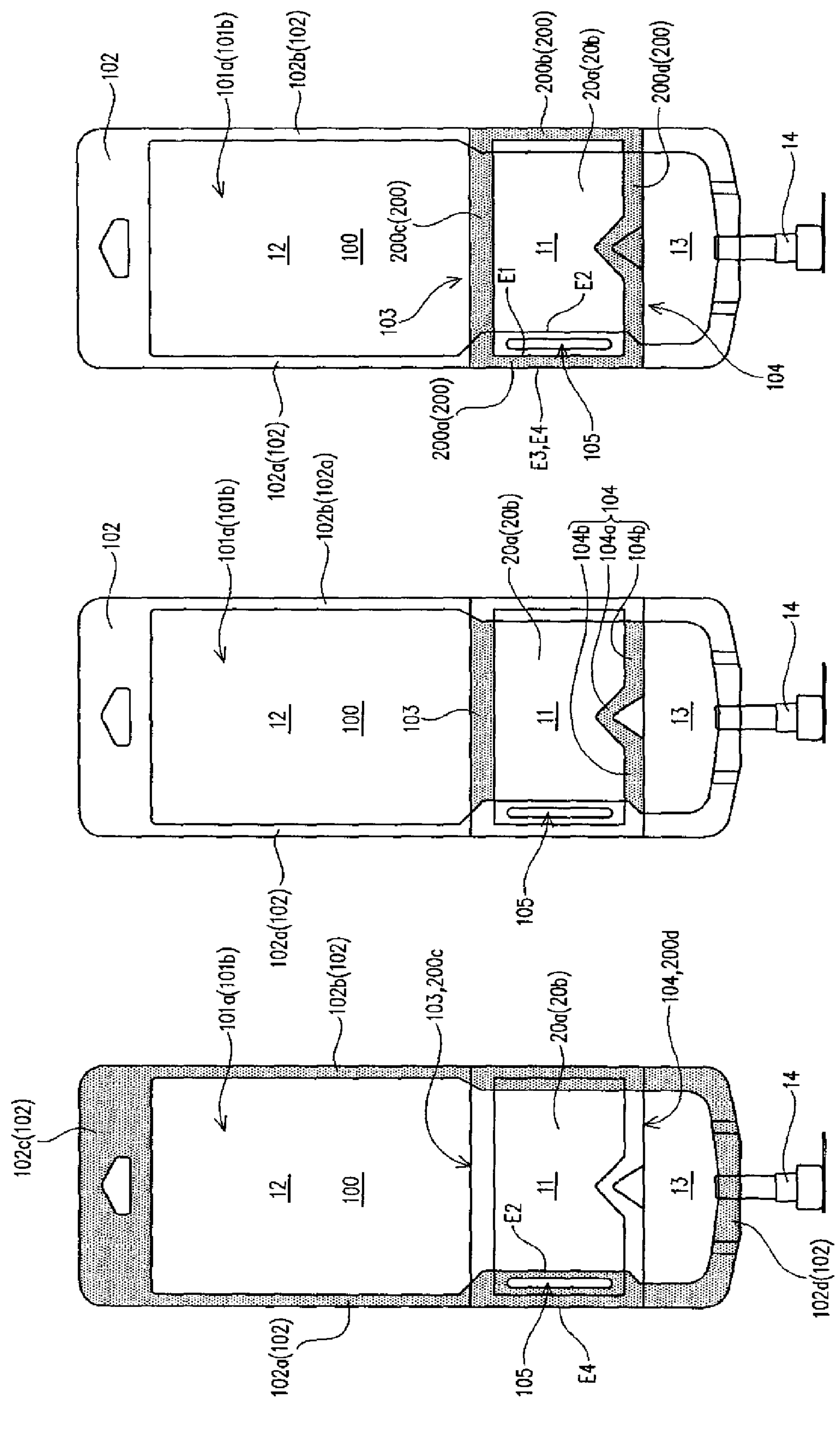
FIG. 13 are explanatory views of the multi-chamber bag of the second embodiment, in which FIG. 13(*a*) is a front view with a strong seal part joining the sheet members together being exaggerated, FIG. 13(*b*) is a front view with weak seal parts (a second weak seal part and a second weak seal part) separably joining the sheet members together being exaggerated, and FIG. 13(*c*) is a front view with an outside seal part joining a cover sheet to a bag body being exaggerated.

As illustrated in FIG. 13(*a*), in the multi-chamber bag 1 of this embodiment, the strong seal part 102 includes, in the same manner as the first embodiment, a pair of first strong seal parts 102*a*, 102*b* formed along the opposite lateral ends with a space therebetween, thereby defining the interior space 100, and a pair of second strong seal parts 102*c*, 102*d* formed to join together the opposite ends of the pair of first strong seal parts 102*a*, 102*b*. In this embodiment, the outer peripheral ends of the rectangular sheet members 101*a*, 101*b* are joined together, thereby forming the strong seal part 102, and therefore the pair of first strong seal parts 102*a*, 102*b* and the pair of second strong seal parts 102*c*, 102*d* together define a substantially rectangular shape of the interior space 100 as viewed from the front side.

Portions of the pair of first strong seal parts 102*a*, 102*b*, which define the medicinal-substance accommodation chamber 11 and the unoccupied chamber 13, are wider than the portions thereof defining the medicinal-solution accommodation chamber 12. A portion of the one first strong seal part 102*a* defining the medicinal-substance accommodation chamber 11 is wider than a portion thereof defining the unoccupied chamber 13. As illustrated in FIG. 13(*c*), the one first outside seal part 200*a* of the pair of the first outside seal parts 200*a*, 200*b* on the one lateral side has an inside edge E1 located outward of the inside edge E2 of the strong seal part 102 (the first strong seal part 102*a*) defining the medicinal-substance accommodation chamber 11.

Figure 14A:
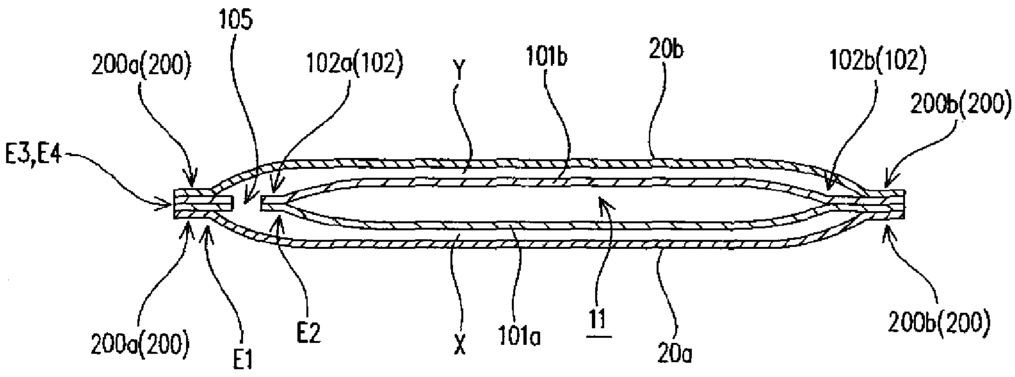
FIG. 14 are cross sectional views of a portion of the multi-chamber bag of the second embodiment, in which FIG. 14(*a*) is a cross sectional view taken along a line G-G in FIG. 12, and FIG. 14(*b*) is a cross sectional view taken along a line H-H in FIG. 12.
Figure 14B:
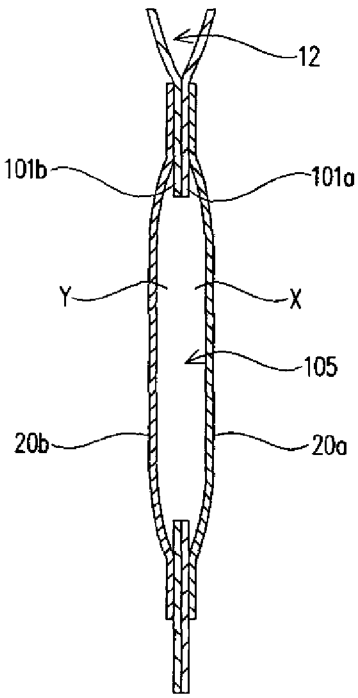
Figure 15B:
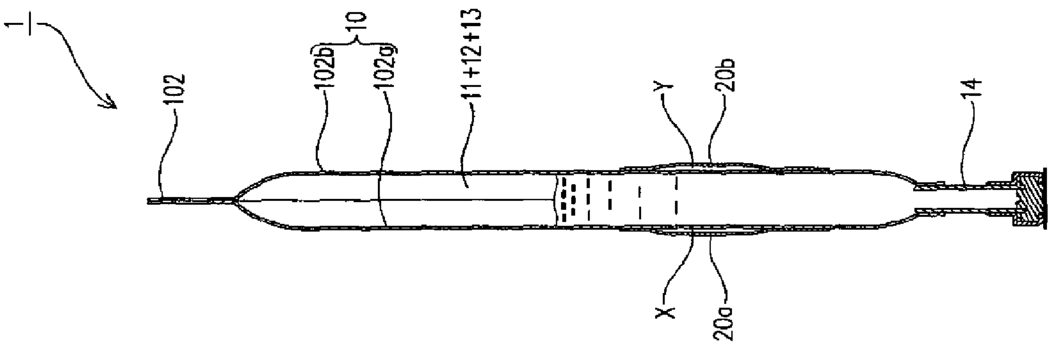
FIG. 15 are explanatory views of the multi-chamber bag of the second embodiment, in which FIG. 15(*a*) is a front view illustrating the bag with a medicinal substance and a diluting solution accommodated therein, and FIG. 15(*b*) is a cross sectional view taken along a vertical axis of the bag with weak seal parts (a first weak seal part and a second weak seal part) ruptured and hence the respective chambers held in communication with each other.
Figure 15A:
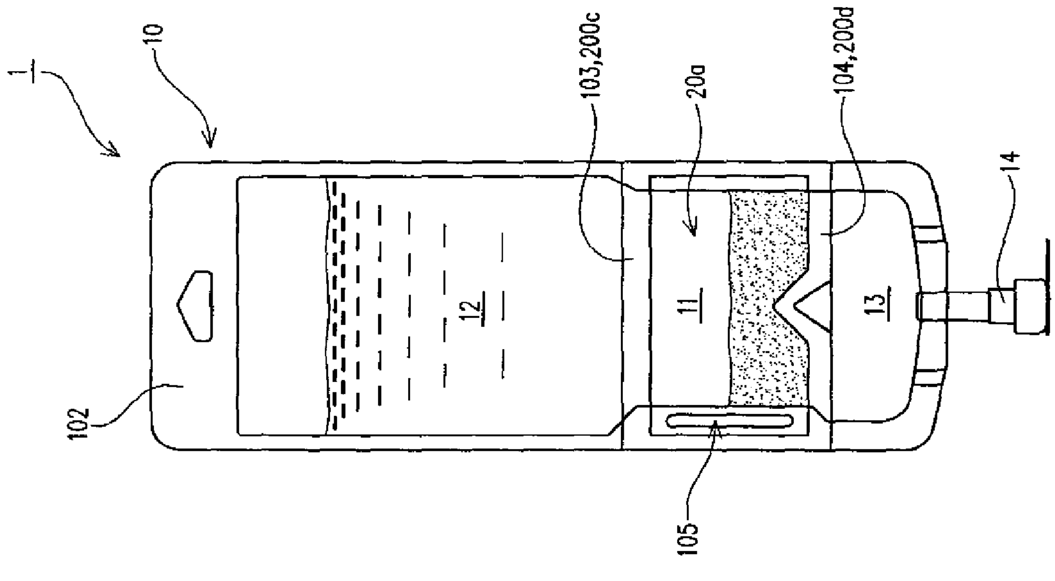

A wider portion of the one first strong seal part 102*a*, which defines the medicinal-substance accommodation chamber 11, (between the inside edge E1 of the first outside seal part 200*a* and the inside edge E2 of the strong seal part 102 (the first strong seal part 102*a*) defining the medicinal-substance accommodation chamber 11) has an opening as the communication part 105. The communication part 105 (the opening) is formed by an elongated hole extending in a direction in which the first strong seal part 102*a* extends. Whereby, as illustrated in FIGS. 14(*a*), 14(*b*), in the same manner as in the case in which the communication part 105 is formed by plural holes 105' . . . in the first embodiment, it is possible to communicate the first space X with the second space Y via the elongated hole 105 while holding the medicinal-substance accommodation chamber 11 under sealed condition, and allow moisture, which has intruded into the first space X as passing through the one cover sheet 20*a*, to flow into the second space Y and hence to be absorbed by the other cover sheet 20*b* defining the second space Y.

As described above, in the multi-chamber bag 1 of this embodiment, in the same manner as the first embodiment, the one sheet member 101*a* and the one cover sheet 20*a* are formed by transparent sheets, and therefore it is possible to securely check the conditions of the medicinal substance at a glance without the necessity to perform a troublesome work, such as peeling of the cover sheet 20*a*. Also, the communication part 105 for communication between the first space X formed between the one sheet member 101*a* and the one cover sheet 20*a* and the second space Y formed between the other sheet member 101*b* and the other cover sheet 20*b* is formed between the inside edge E1 of the outer seal part 200 on at least one lateral side of the cover sheets 20*a*, 20*b* and the inside edge E2 of the strong seal part 102 on at least one lateral side of the bag body 10. With this arrangement, moisture, which has passed through the one cover sheet 20*a* and intruded into the first space X, flows into the second space and thus can be absorbed by the other cover sheet 20*b* defining the second space Y.

Since the pair of cover sheets 20*a*, 20*b* are imparted with an oxygen barrier property, oxygen, which deteriorates an antibiotic, is unlikely to intrude into the chamber and thus it is possible to prevent deterioration of the antibiotic. Also, in the multi-chamber bag 1 of this embodiment, a light blocking effect is imparted to the other cover sheet 20*b* by providing an aluminium layer thereto. Therefore, when the multi-chamber bag 1 is folded into two with the other cover sheet 20*b* facing outward, light does not directly hit the medicinal-substance accommodation chamber 11 and hence it is possible to prevent deterioration of the antibiotic due to the irradiation of light.

Since the communication part 105 is formed by an elongated hole bored in the strong seal part 102, it is possible to communicate the first space X with the second space Y via the elongated hole 105 while holding the medicinal-substance accommodation chamber 11 under sealed condition.

Now, the description will be made for the multi-chamber bag of the third embodiment of the present invention. The multi-chamber bag of this embodiment is the same as that of the first embodiment except that the position of the communication part for communication between the first space and the second space is different, as illustrated in FIGS. 16 to 22, and therefore elements identical or corresponding to those of the first embodiment are allocated the same names and the same reference codes to omit the description thereof, while the different elements or members will be mainly described.

Figure 16A:
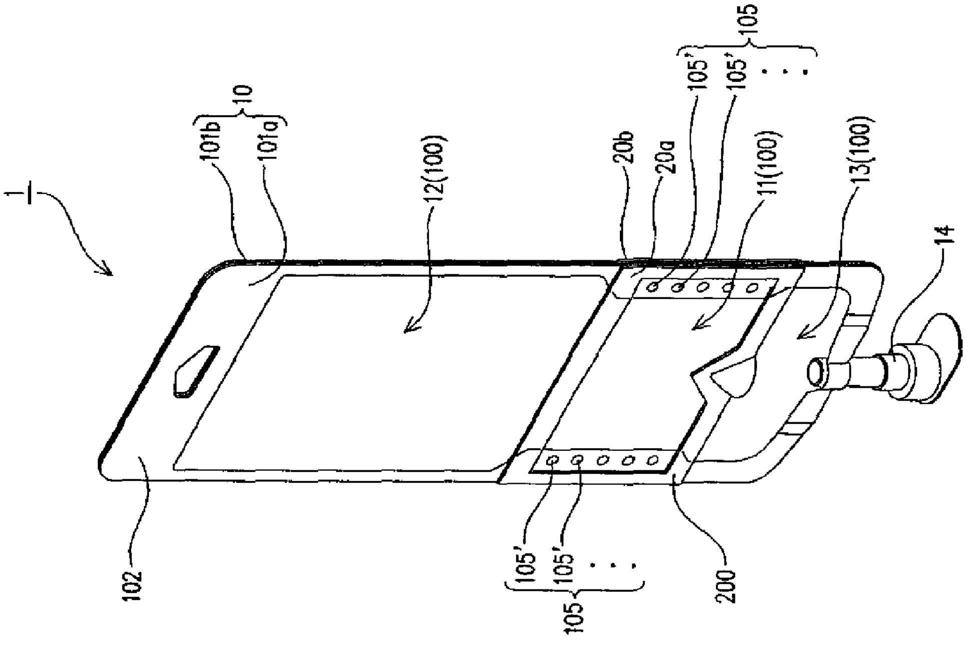
FIG. 16 are explanatory views of the multi-chamber bag of a third embodiment of the present invention, in which FIG. 16(*a*) is an entire perspective view, and FIG. 16(*b*) is an exploded perspective view.
Figure 16B:
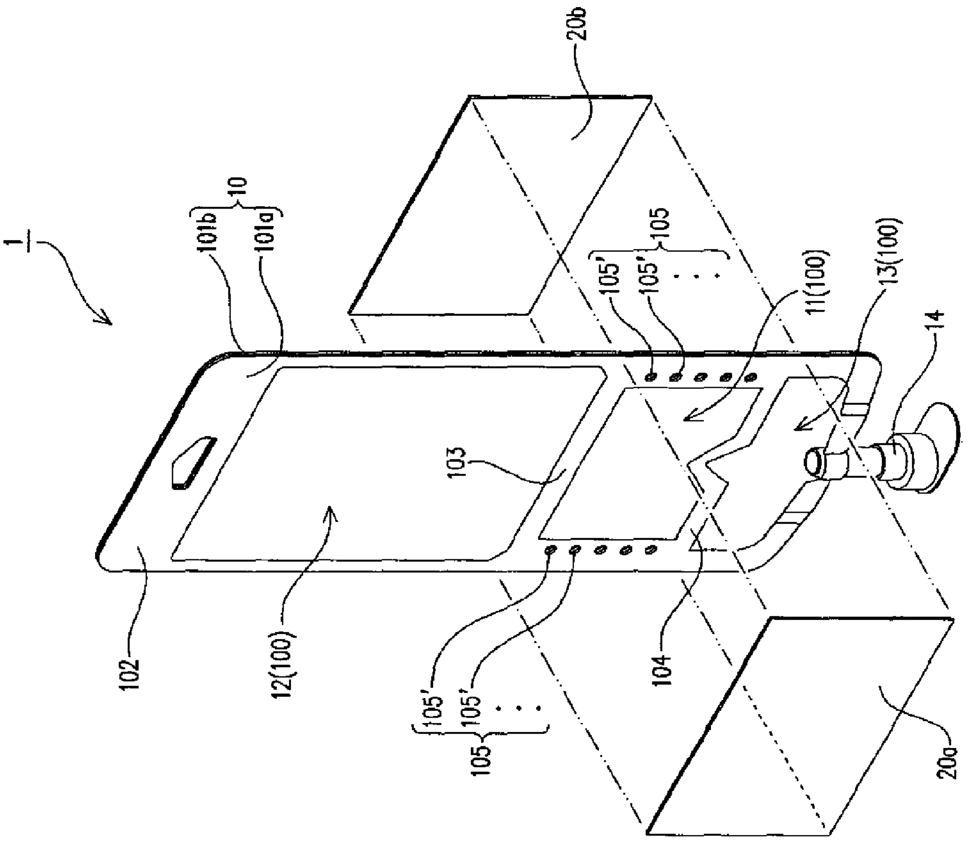
Figures 20A, 20B, 20C:
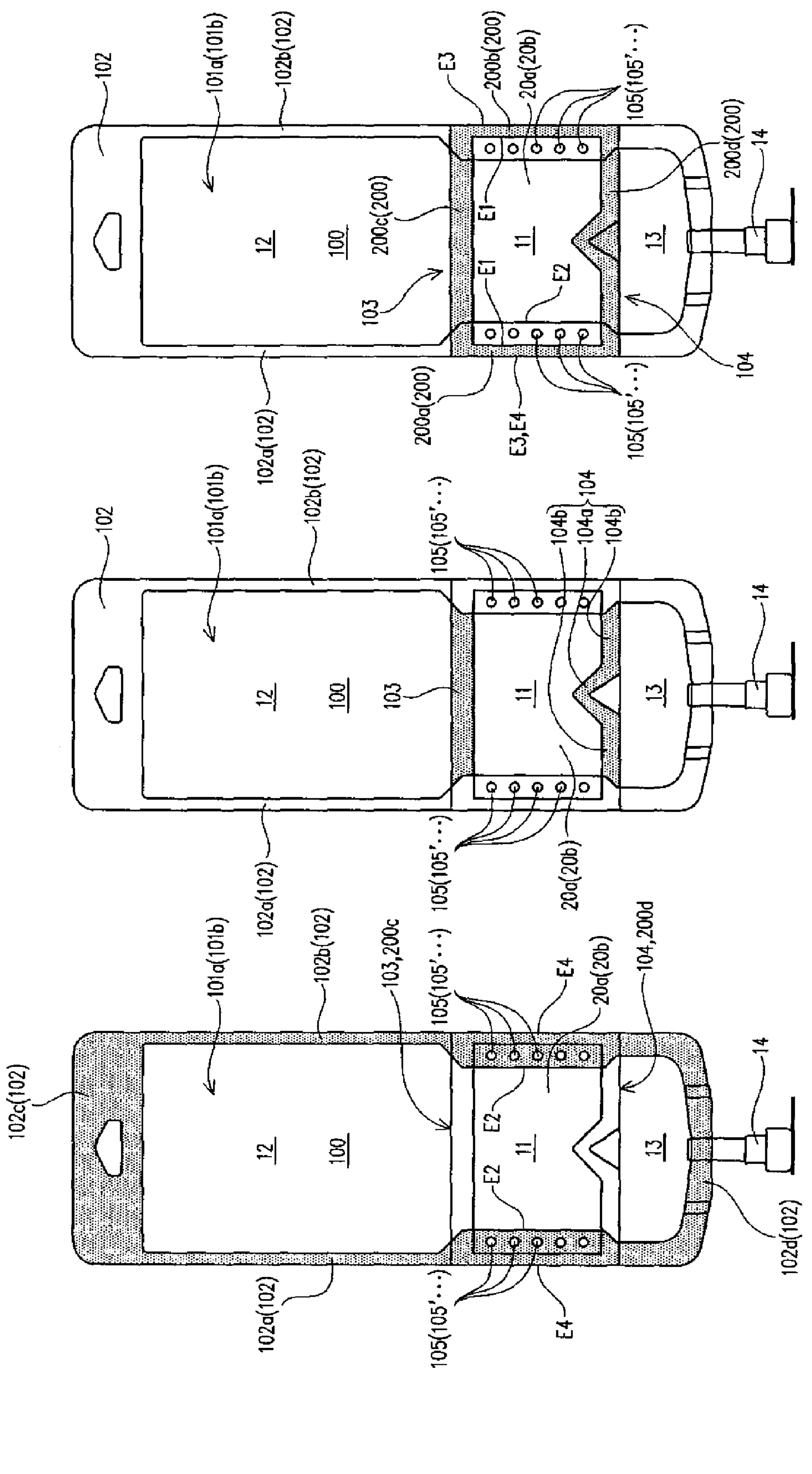
FIG. 20 are explanatory views of the multi-chamber bag of the third embodiment, in which FIG. 20(*a*) is a front view with a strong seal part joining the sheet members together being exaggerated, FIG. 20(*b*) is a front view with weak seal parts (a third weak seal part and a third weak seal part) separably joining the sheet members together being exaggerated, and FIG. 20(*c*) is a front view with an outside seal part joining a cover sheet to a bag body being exaggerated.

As illustrated in FIG. 16, the multi-chamber bag 1 of this embodiment has communication parts 105 for communication between the first space X and the second space Y on the opposite lateral sides of the medicinal-substance accommodation chamber 11. Specifically, as illustrated in FIG. 20(*a*), the strong seal part 102 of this embodiment includes a pair of first strong seal parts 102*a*, 102*b* formed along the opposite lateral ends with a space therebetween, thereby defining the interior space 100, and a pair of second seal parts 102*c*, 102*d* formed to join together the opposite ends of the pair of first strong seal parts 102*a*, 102*b*. Portions of the pair of first strong seal parts 102*a*, 102*b*, which define the medicinal-substance accommodation chamber 11, are wider than the portions thereof respectively defining the medicinal-solution accommodation chamber 12 and the unoccupied chamber 13.

Openings 105' of the communication part 105 are bored in wider portions of the first strong seal parts 102*a*, 102*b* defining the medicinal-substance accommodation chamber 11. In the same manner as the first embodiment, the communication parts 105 each are formed of plural openings 105' . . . spaced apart from each other in a direction in which the first strong seal part 102*a* extends. The openings 105' . . . each are formed into a round hole.

Figures 17A, 17B, 17C:
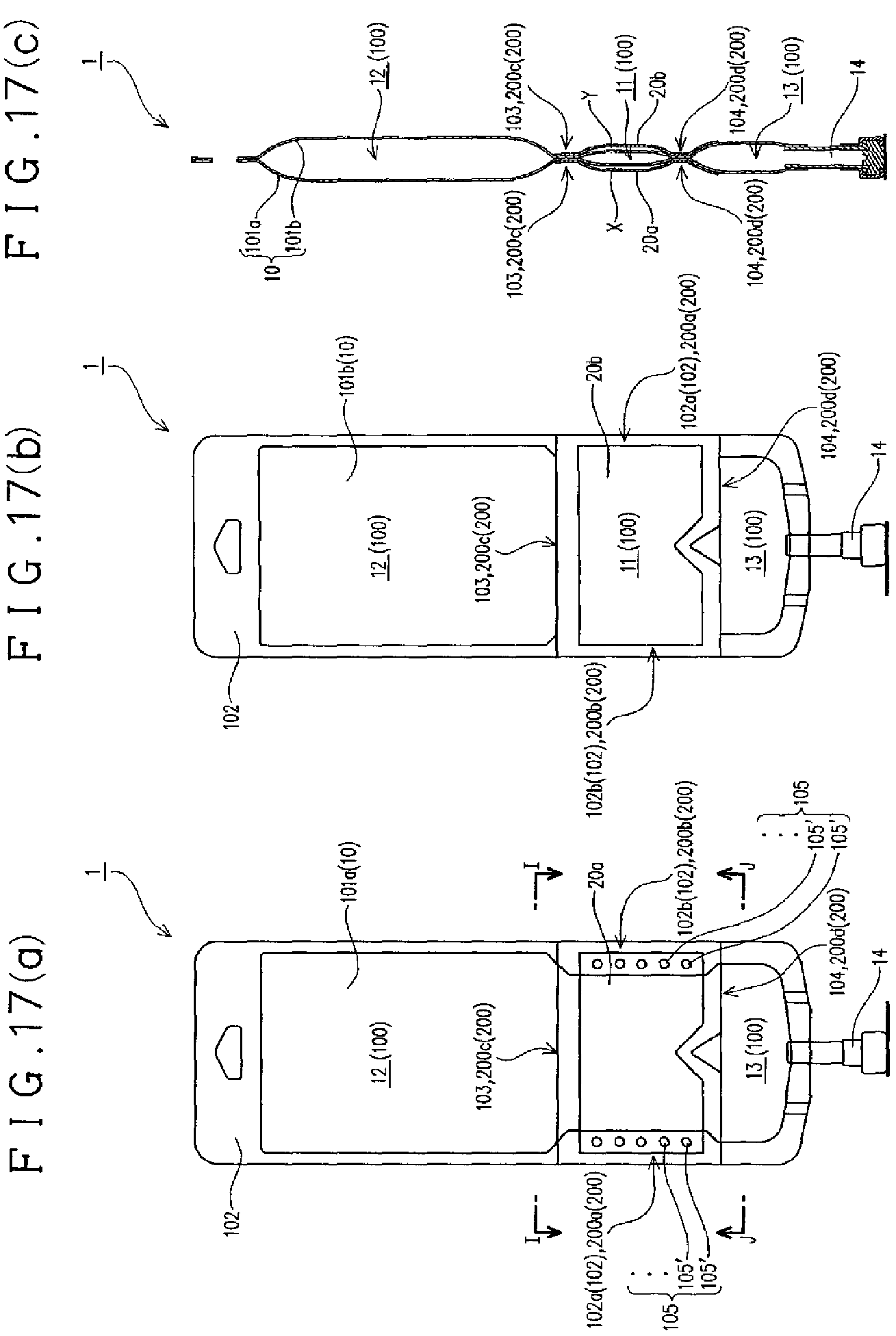
FIG. 17 are explanatory views of the multi-chamber bag of the third embodiment, in which FIG. 17(*a*) is a front view with a medicinal substance and a diluting solution chamber omitted, FIG. 17(*b*) is a rear view with a medicinal substance and a diluting solution chamber omitted, and FIG. 17(*c*) is a cross sectional view taken along a vertical axis of the bag.
Figure 18C:
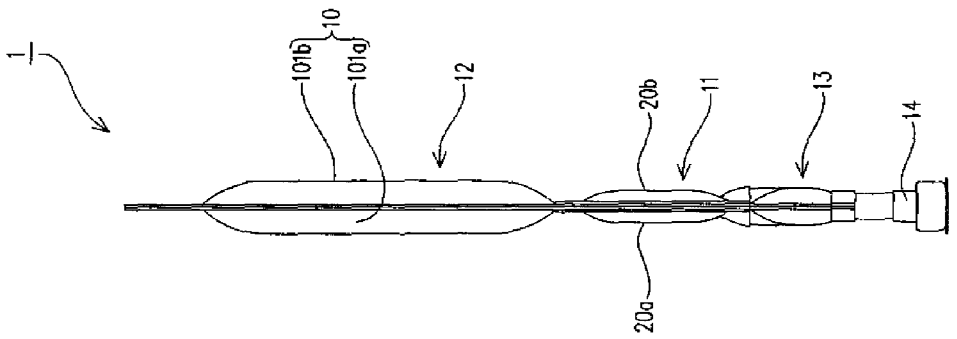
FIG. 18 are explanatory views of the multi-chamber bag of the third embodiment, in which FIG. 18(*a*) is a plan view, FIG. 18(*b*) is a bottom view and FIG. 18(*c*) is a side view.
Figure 18A:
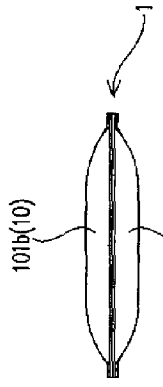
Figure 18B:
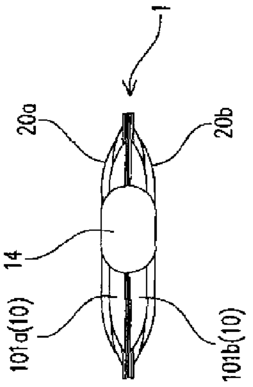

The one cover sheet 20*a* is overlaid onto the one sheet member 101*a* so as to cover the medicinal-substance accommodation chamber 11, as illustrated in FIG. 17(*a*), and the other cover sheet 20*b* is overlaid onto the other sheet member 101*b* so as to cover the medicinal-substance accommodation chamber 11, as illustrated in FIG. 17(*b*). As illustrated in FIG. 20(*c*), the outside seal part 200 includes a pair of first outside seal parts 200*a*, 200*b* corresponding to the pair of first strong seal parts 102*a*, 102*b*, and a pair of second outside seal parts 200*c*, 200*d* corresponding to the first weak seal part 103 and the second weak seal part 104. The pair of first outside seal parts 200*a*, 200*b* each are formed so as to have the inside edge E1 located outward of the inside edge E2 of the strong seal part 102 (the first strong seal parts 102*a*, 102*b*) defining the medicinal-substance accommodation chamber 11.

Figure 19:
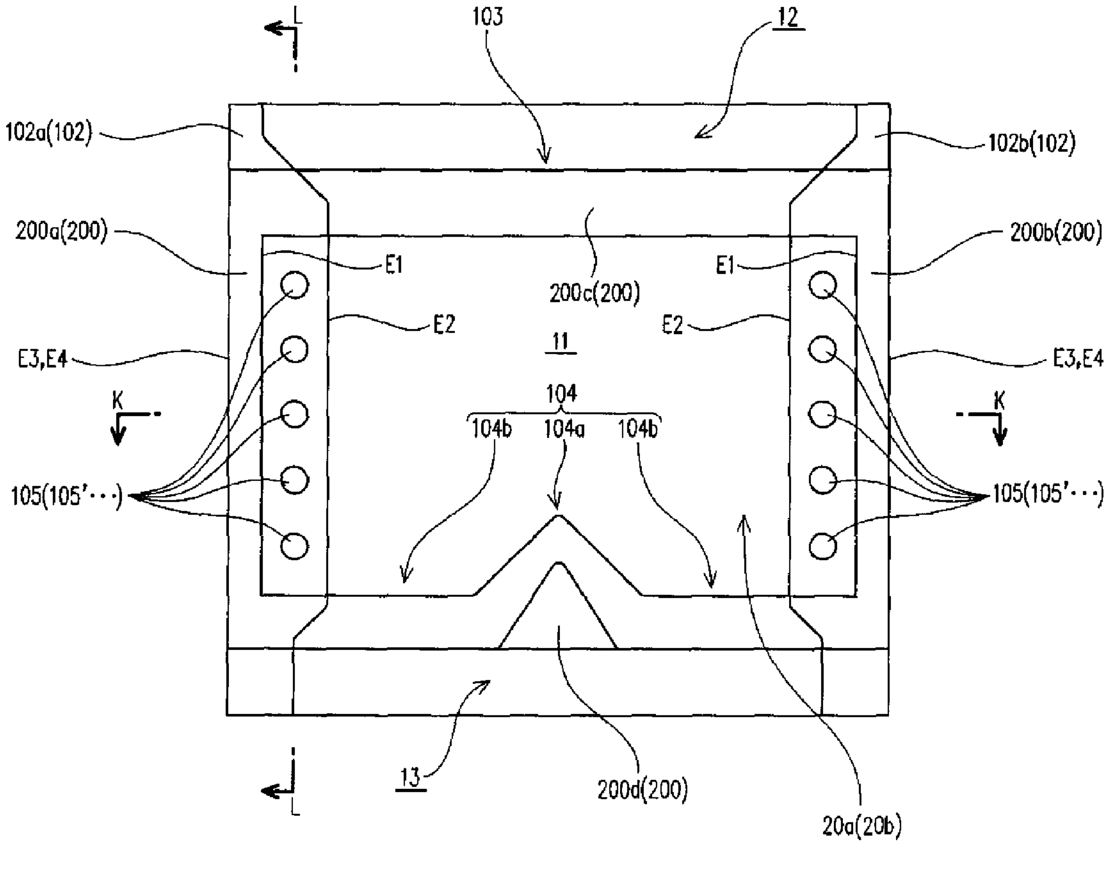
FIG. 19 is a partially enlarged view of a portion I-J in FIG. 17(*a*) of the multi-chamber bag of the third embodiment.

As illustrated in FIG. 19, since the cover sheets 20*a*, 20*b* of this embodiment are formed with a size and a shape corresponding to the area defined by the outside edges of the pair of first strong seal parts 102*a*, 102*b*, the first weak seal part 103 and the second weak seal part 104, when the outside edges E3 of both the first outside seal parts 200*a*, 200*b* are aligned with outside edges E4 of the first strong seal parts 102*a*, 102*b* (the lateral ends of the sheet members 101*a*, 101*b*), as illustrated in FIG. 20(*c*), they have a width narrower than the corresponding first strong seal parts 102*a*, 102*b* and are overlapped to the first strong seal parts 102*a*, 102*b*.

Whereby the pair of first outside seal parts 200*a*, 200*b* are formed so as to detour the communication parts 105 formed in the first strong seal parts 102.

Figure 21A:
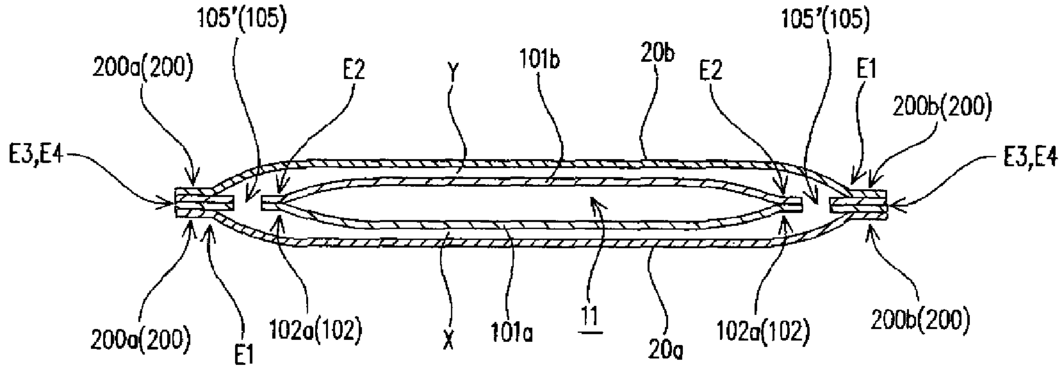
FIG. 21 are cross sectional views of a portion of the multi-chamber bag of the third embodiment, in which FIG. 21(*a*) is a cross sectional view taken along a line K-K in FIG. 19, and FIG. 21(*b*) is a cross sectional view taken along a line L-L in FIG. 19.
Figure 21B:
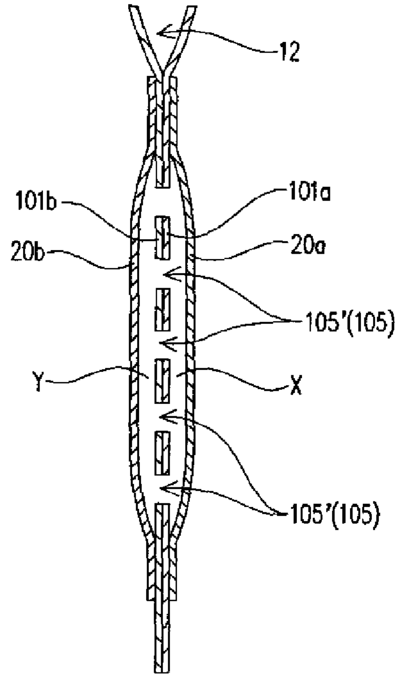
Figure 22B:
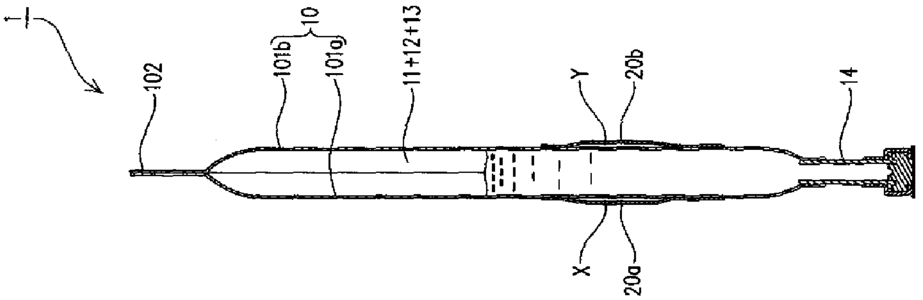
FIG. 22 are explanatory views of the multi-chamber bag of the third embodiment, in which FIG. 22(*a*) is a front view illustrating the bag with a medicinal substance and a diluting solution accommodated therein, and FIG. 22(*b*) is a cross sectional view taken along a vertical axis of the bag with weak seal parts (a third weak seal part and a third weak seal part) ruptured and hence the respective chambers held in communication with each other.
Figure 22A:
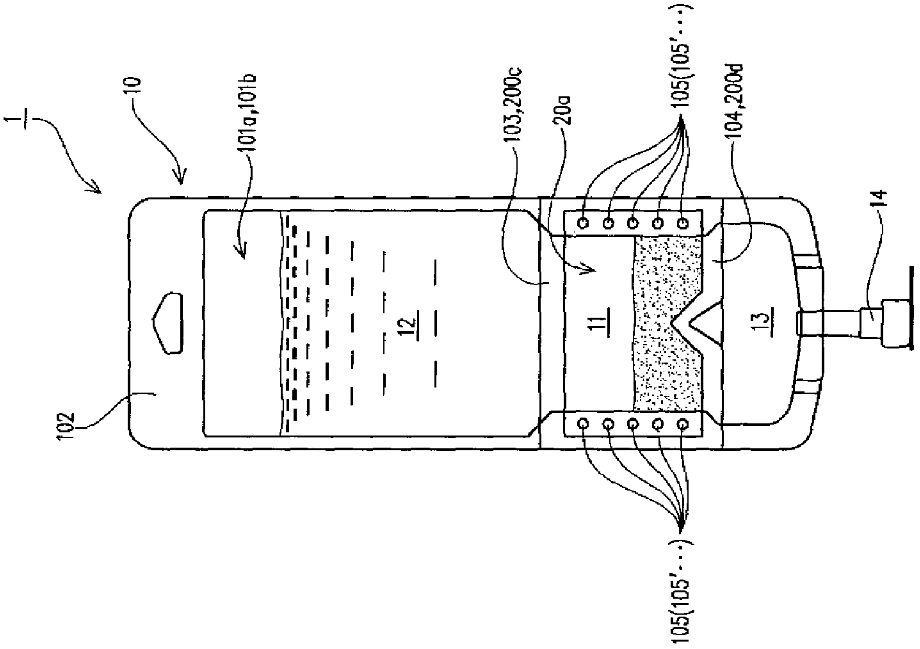

As illustrated in FIGS. 17(*c*) and 21(*a*), the pair of cover sheets 20*a*, 20*b* are joined to the bag body 10 (the sheet members 101*a*, 101*b*) so that the first space X is defined between the one sheet member 101*a* (the bag body 10) and the one cover sheet 20*a*, while the second space Y is defined between the other sheet member 101*b* (the bag body 10) and the other cover sheet 20*b*. As illustrated in FIGS. 21(*a*) and 21(*b*), the first space X and the second space Y are communicated with each other via the communication parts 105 (the holes 105) formed between the inside edges E1, E1 of the pair of first outside seal parts 200*a*, 200*b* and the inside edges E2, E2 of the pair of first strong seal parts 102*a*, 102*h*. Whereby, in the multi-chamber bag 1 of this embodiment, too, it is possible to allow moisture, which has passed through the one cover sheet 20*a* and intruded into the first space X, to flow into the second space Y, and hence to be absorbed by the other cover sheet 20*b* defining the second space Y.

As described above, according to the multi-chamber bag 1 of this embodiment, since the one sheet member 101*a* and the one cover sheet 20*a* are formed by transparent sheets in the same manner as the first and second embodiments, it is possible to securely check the conditions of the medicinal substance at a glance without the necessity to perform a troublesome work, such as peeling of the cover sheet 20*a*. The communication parts 105 for communication between the first space X between the one sheet member 101*a* and the one cover sheet 20*a* and the second space Y between the other sheet member 101*b* and the other cover sheet 20*b* are formed between the inside edges E1, E1 of the outside seal parts 200 (the pair of first outside seal parts 200*a*, 200*b*) on the opposite lateral ends of the cover sheets 20*a*, 20*b* and the inside edges E2, E2 of the strong seal parts (the pair of first strong seal parts 102*a*, 102*b*) on the opposite lateral ends of the bag body 10. With this arrangement, it is possible to allow moisture, which has passed through the one cover sheet 20*a* and intruded into the first space X, to flow into the second space Y and thus to be absorbed by the second cover sheet 20*b* defining the second space Y.

Since the pair of cover sheets 20*a*, 20*b* are imparted with an oxygen barrier property, oxygen that deteriorates an antibiotic is unlikely to pass therethrough, and thereby the antibiotic can be prevented from being deteriorated. The multi-chamber bag 1 of this embodiment is imparted with a light blocking effect by providing an aluminium layer to the other cover sheet 20*b*. With this arrangement, when the multi-chamber bag 1 is folded into two with the other cover sheet 20*b* facing outward, light does not directly hit the medicinal-substance accommodation chamber 11 and hence it is possible to prevent deterioration of the antibiotic due to the irradiation of light.

The communication parts 105 each are formed of plural holes 105' . . . bored in the strong seal parts 102, and therefore the first space X and the second space Y can be communicated with each other via the holes 105' . . . while holding the medicinal-substance accommodation chamber 11 under sealed condition. Also, in this embodiment, since the pair of communication parts 105 are formed on the opposite lateral sides of the bag body 10, it is possible to allow moisture, which has intruded into the first space X, to be securely drawn into the second space Y and thus to be absorbed by the other cover sheet 20*b*.

EXAMPLES

In order to confirm the performance of the multi-chamber bag of the present invention, the present inventors had conducted performance testings following the conditions mentioned below.

<Structure of Multi-Chamber Bag>

Mode of the multi-chamber bag: Multi-chamber bag of the first embodiment (cf. FIG. 1)

Sheet members 101*a*, 101*b* of the bag body 10:

Laminate sheets of PE (20 μm), PE+PE elastomer (60 μm), COP+PE (10 μm), PE elastomer+PE (60 μm) and PE+PP (30 μm) (a layer of PE (20 μm) is located on the outside.)

Pair of cover sheets 20*a*, 20*b*:

One cover sheet (transparent cover sheet) 20*a*:

Laminate sheet of alumina-deposited PET (12 μm), alumina-deposited PET (12 μm), alumina-deposited PET (12 μm) and PP (50 μm) (moisture penetration rate of 0.058): (a layer of the alumina-deposited PET (12 μm) is located on the outside.)

Other cover sheet (cover sheet having a light blocking effect) 20*b*:

Laminate sheet of PET (12 μm), aluminum foil (9 μm), CaO (50%)-containing PE (30 μm) and PP (10 μm) (moisture penetration rate of 0): (a layer of PET (12 μm) is located on the outside.)

Distance A between the pair of first outside seal parts 200*a*, 200*b*: 90 mm Distance B between the pair of second outside seal parts 200*c*, 200*d*: 62 mm Shape of a portion corresponding to the easy-to-open part 104*a* of the second outside seal part 200*d*: triangular shape Size of a portion corresponding to the easy-to-open part 104*a* of the second outside seal part 200*d*:

Length of the bottom side (length in which the second outside seal part extends) W: 23 mm Height (projecting amount towards the medicinal-substance accommodation chamber 11: H): 9 mm Cover area (area of an unsealed portion surrounded by the first outside seal parts 200*a*, 200*b* and the second outside seal parts 200*c*, 200*d*):

$$(A\times B)-(W\times H)\times 0.5=(90\text{ mm}\times 62\text{ mm})-(23\text{ mm}\times 9\text{ mm})\times 0.5=5476.5\text{ mm}^2$$

Shape of the opening 105' of the communication part 105: round

Size d of the opening 105': 4 mm in diameter

Number of the openings 105': 5

Area of the communication part 105:

$$\pi/4\times d^2\times 5\text{ parts}=\pi/4\times(4\text{ mm})^2\times 5\text{ parts}=62.8\text{ mm}^2$$

Ratio of the opening area of the communication part 105 to the cover area: 62.8 mm$^2$/5476.5 mm$^2$=0.011467 (1.1%)

Object of the medicinal-substance accommodation chamber 11: powdered cefozopran <Measurement of Moisture of Object within Medicinal-Substance Accommodation Chamber>

Following the Karl-Fischer's method

The multi-chamber bag of the above structure was left for 14 days and then the moisture content of the object (powdered cefozopran) was measured by the Karl-Fischer's method. The moisture content of the accommodated object was 1.95%.

The present inventors overlapped a pair of sheets made of the same material as that of the bag body 10 (the sheet members 101*a*, 101*b*) of the above Example together, sealed the outer periphery thereof to form a bag having the same size as the medicinal-substance accommodation chamber 11, accommodated the powdered cefozopran in the bag, overlapped thereto a pair of sheets made of the same material as that of the pair of cover sheets 20*a*, 20*b* of the Example, sealed the outer periphery thereof to form a bag, placed the bag with the powdered cefozopran accommodated therein, thereby preparing a sample, in which the one cover sheet 20*a* is held in communication with the other cover sheet 20*b* throughout the entire outer circumference of the medicinal-substance accommodation chamber 11. The sample was left for 14 days and then the moisture content of the accommodated object (powdered cefozopran) of the sample was measured by the Karl-Fischer's method. As a result, the moisture content of the accommodated object of the sample was 1.93%. It was confirmed that when powdered cefozopran accommodated in a bag made of the same material as that of the bag body 10 was left to stand, the powdered cefozopran absorbed moisture and hence was deteriorated.

Thus, it was found that the multi-chamber bag can efficiently absorb moisture existing around the medicinal-substance accommodation chamber 11 by the cover sheet 20*b*, in the same manner as the sample, in which the communication of moisture, gasses and the like can be smoothly made throughout the entire circumference of the inside bag. That is, with the opening area of the communication part 105 being 1% or more of the cover area, it could be confirmed that the absorption of adverse influence causing matters can be efficiently made while securing the medicinal-substance accommodation space in the medicinal-substance accommodation chamber. The moisture percentage which can suppress the deterioration of a medicinal substance varies depending on the medicinal substance accommodated in the medicinal-substance accommodation chamber 11. However, generally it is preferable to reduce the moisture content of an accommodated object (medicinal substance) to 2.5% or lower, and it could be also confirmed that the moisture absorption by employing the cover sheet 20*b* is actually effected.

The multi-chamber bag of the present invention is not necessarily limited to any one of the above embodiments, and it is a matter of course that the multi-chamber bag of the present invention can be changed or modified within the scope of the present invention.

In the above embodiments, a powdered antibiotic was cited as a medicinal substance to be accommodated in the medicinal-substance accommodation chamber 11 without intention to limit the present invention. For example, a liquid medicinal substance may be accommodated. In the above embodiments, since an antibiotic was employed as a medicinal substance to be accommodated in the medicinal-substance accommodation chamber 11, oxygen and moisture were targeted as adverse influence causing matters, which deteriorates the medicinal substance. However, the present invention is not necessarily limited thereto. The other cover sheet 20*b* is correspondingly designed so as to be able to absorb each adverse influence causing matter, which deteriorates or change the color of a medicinal substance to be accommodated in the medicinal-substance accommodation chamber 11. The above embodiments were described by taking, for example, a case in which a diluting solution for diluting the medicinal substance accommodated in the medicinal-substance accommodation chamber 11 is employed as a medicinal solution, and the medicinal-solution accommodation chamber is employed as the medicinal-solution accommodation chamber 12. However, the medicinal solution accommodated in the medicinal-solution accommodation chamber 12 is not necessarily limited to a diluting solution, while it is possible to employ a liquid medicinal substance to be mixed with the medicinal substance accommodated in the medicinal-substance accommodation chamber 11.

In the above embodiments, the interior space 100 formed by joining the two sheet members 101*a*, 101*b* is partitioned into three compartments respectively serving as the medicinal-substance accommodation chamber 11, the diluting-solution accommodation chamber (medicinal-solution accommodation chamber) 12 and the unoccupied chamber 13. The present invention is not necessarily limited thereto. For example, it is possible to employ an arrangement, in which the interior space 100 is partitioned into two compartments respectively serving as the medicinal-substance accommodation chamber 11 and the medicinal-solution accommodation chamber 12, and the port member 14 is connected to any one of the medicinal-substance accommodation chamber 11 and the medicinal-solution accommodation chamber 12. In this case, too, the medicinal-substance accommodation chamber 11 and the medicinal-solution accommodation chamber 12 can be separated from each other by the rupturable weak seal part 103 (corresponding to the first weak seal part 103). In the above embodiments, the medicinal-substance accommodation chamber 11 is arranged at an intermediate position with the medicinal-solution accommodation chamber 12 and the unoccupied chamber 13 formed on the opposite sides of the medicinal-substance accommodation chamber 11. In this respect, for example, it is possible to employ an arrangement, in which the medicinal-solution accommodation chamber 12 is arranged at an intermediate position with the medicinal-substance accommodation chamber 11 and the unoccupied chamber 13 formed on the opposite sides of the medicinal-solution accommodation chamber 12. However, considering the secured dilution for a medicinal substance, those chambers are preferably arranged in the same manner as the above embodiments.

In the first and third embodiments, each opening 105' of the communication part 105 is formed into a round hole without intention to limit the present invention thereto. For example, it is possible to employ holes of a polygonal shape, such as a triangular shape and a rectangular shape. In the first and third embodiments, the communication part 105 is formed of plural openings 105' . . . without intention to limit the present invention thereto. The opening of the communication part 105 may be formed into an elongated hole in the same manner as the second embodiment.

Figure 23A:
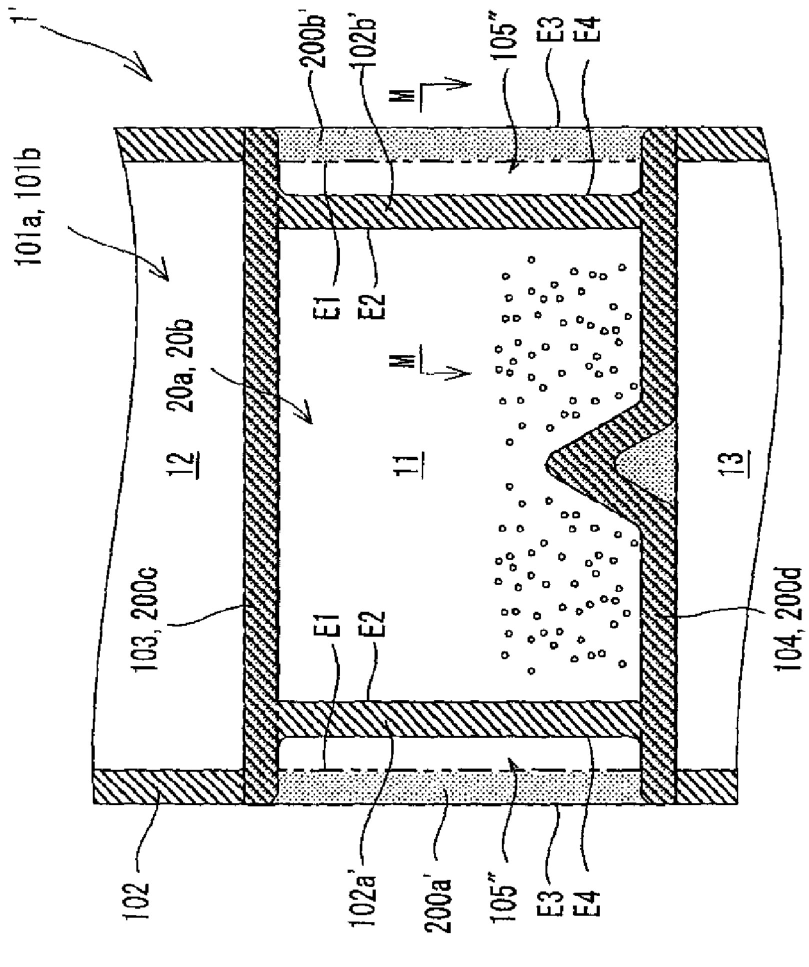
FIG. 23 are explanatory views of the multi-chamber bag of another embodiment of the present invention, in which FIG. 23(*a*) is a partially enlarged front view with a strong seal part and weak seal parts exaggerated by diagonal lines and outside seal parts exaggerated by stippling, and FIG. 23(*b*) is a cross sectional view taken along a line M-M in FIG. 23(*a*).
Figure 23B:
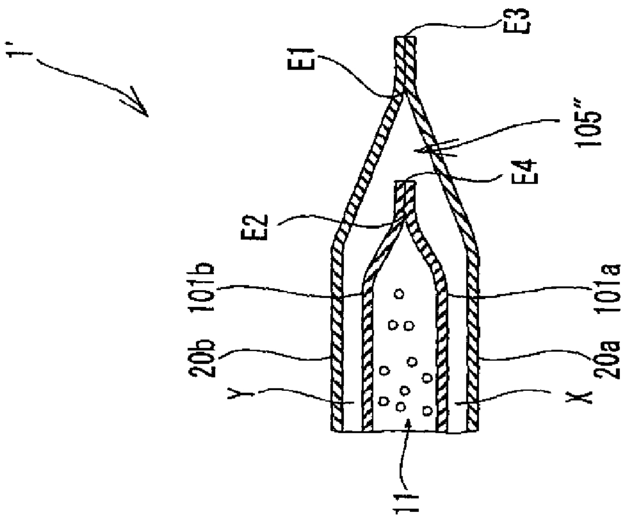

In the above embodiments, the communication part 105 is formed by an opening provided in the first strong seal parts 102*a*, 102*b* without intention to limit the present invention thereto. For example, as illustrated in FIG. 23(*a*), the first outside seal part 102' is formed so as to have each inside edge E2 and each outside edge E4 located closer to the medicinal-substance accommodation chamber 11 than the corresponding inside edge E1 of the first outside seal parts 200*a*', 200*b*', and ends of the cover sheets 20*a*, 20*b* protruding outwards from the sheet members 101*a*, 101*b* are joined together to form the first outside seal parts 200*a*', 200*b*' and the both ends of the cover sheets 20*a*, 20*b* are joined to the bag body 10 to form the second outside seal part 200*c*'. Thus, the first space X and the second space Y can be formed between the sheet members 101*a*, 101*b* and the cover sheets 20*a*, 20*b*, and gaps are formed between the inside edges E1 of the first outside seal parts 200*a*', 200*b*' and the outside edges E4 of the first strong seal parts 102'.

Accordingly, as illustrated in FIG. 23(*b*), the gaps formed between the inside edges E1 of the first outside seal parts 200*a*', 200*b*' and the inside edges E2 (the outside edges E4) of the first strong seal parts 102' are served as the communication parts 105" for communication between the first space X between the one sheet member 101_a_ and the one cover sheet 20_a_ and the second space Y between the other sheet member 101_b_ and the other cover sheet 20_b_. Whereby, it is possible to allow adverse influence causing matters, which has passed through the one cover sheet 20_a_ and intruded into the first space X, to flow into the second space Y and hence to be absorbed by the other cover sheet 20_b_ defining the second space Y. With this arrangement, in which the communication parts 105" are formed by the gaps that are formed between the inside edges E1 of the first outside seal parts 200_a_', 200_b_' and the outside edges E4 of the first strong seal parts 102_a_', 102_b_', it is possible to provide a multi-chamber bag that is capable of producing the above functions and effects without the necessity to perform a step of forming openings (holes) as the communication parts 105 in the first strong seal parts 102_a_', 102_b_'.

In the above embodiments, moisture as an adverse influence causing matter is absorbed by the other cover sheet 20_b_ with absorbent for absorbing moisture kneaded therein. Alternatively, for example, it is possible to directly or indirectly provide absorbent for absorbing adverse influence causing matters in an inner surface facing the bag body 10. That is, it is possible to employ an arrangement in which absorbent is placed in a bag and bonded to the inner surface of the other cover sheet 20_b_, or an arrangement in which absorbent is laminated onto the inner surface of the other cover sheet 20_b_.

In the above embodiments, the pair of cover sheets 20_a_, 20_b_ are imparted with an oxygen barrier property. However, for example, when the one cover sheet 20_a_ allows such an amount of gas as to deteriorate a medicinal substance to pass therethrough, the other cover sheet 20_b_ may be provided with absorbent for absorbing the gas (e.g., deoxidant). With this arrangement, too, it is possible to prevent gas deteriorating the medicinal substance from reaching the inside of the medicinal-substance accommodation chamber 11, and hence prevent the deterioration of the medicinal substance in the same manner as the above embodiments. When the cover sheet 20_a_ allows both such an amount of gas and such an amount of moisture as to deteriorate a medicinal substance to pass therethrough, absorbent for absorbing the gas and moisture absorbent may be used in combination, and a medicinal substance accommodated in the medicinal-substance accommodation chamber 11 is not necessarily limited to powdered substance, but it is possible to employ liquid substance.

In the above embodiments, both the two sheet members 101_a_, 101_b_ of the bag body 10 are transparent without intention to limit the present invention thereto. It is a matter of course to form the other sheet member 101_b_ by an opaque sheet. Even with this arrangement, it is possible to check the condition of a medicinal substance since the one sheet member 101_a_ is transparent.

In the above embodiments, the pair of cover sheets 20_a_, 20_b_ respectively have different structures. In this respect, for example, it is possible to employ an arrangement, in which the other cover sheet 20_b_ is imparted with an absorbing capacity for absorbing adverse influence causing matters while the basic structure is commonly shared by the pair of cover sheets 20_a_, 20_b_.

Specifically, when adverse influence causing matters are moisture and oxygen, it is possible to employ an arrangement, in which the pair of cover sheets 20_a_, 20_b_ each have a basic structure, in which a barrier layer has polyethylene terephthalate (PET) or polyamide vapor deposited with aluminum oxide (alumina) and/or silicon oxide (silica), and the other cover sheet 20_b_ additionally has a layer having moisture absorbent kneaded in a resin material in addition to the above structure and further has a sealant layer. Accordingly, the pair of cover sheets 20_a_, 20_b_ are imparted with a barrier property against oxygen, while the other cover sheet 20_b_ is imparted with a capacity for absorbing moisture.

As described above, when a layer having water absorbent kneaded therein is provided, the moisture absorbent is preferably any one of an inorganic substance selected from calcium oxide, aluminium oxide, zeolite, silica gel, dried alum, magnesium sulfate, calcium chloride, sodium sulfate, potassium sulfate, phosphorus pentoxide, sodium carbonate and calcium carbonate; an organic substance selected from poly(metha)-acrylate, carboxymethylcellulose and polyethyleneglycol; a derivative thereof; a combination of the inorganic substances; a combination of the organic substances; and a combination of the inorganic substance and the organic substance.

A resin material of a sealant layer is preferably any one selected from linear-low-density polyethylene (LLDPE), low-density polyethylene (LDPE), polypropylene (PP), ethylene-vinylacetate copolymer (EVA), acid copolymer, acid ester copolymer and ionomer, or a combination thereof.

Although not mentioned in the second and third embodiments, the opening area of the communication part 105 is preferably set to be 1% to 20% of the area of an unsealed portion (cover area) surrounded by a portion in which the outer peripheries of the cover sheets 20_a_, 20_b_ are sealed to the sheet members 101_a_, 101_b_ (the first outside seal parts 200_a_, 200_b_, and the second outside seal part 200_c_, 200_d_ (cf. FIG. 13(_c_), FIG. 20(_c_)).

The invention claimed is:

1. A multi-chamber bag comprising a bag body that has a strong seal part that joins two sheet members together to define an interior space of the bag body, and a weak seal part that partitions the interior space of the bag body into a medicinal-substance accommodation chamber and a medicinal-solution accommodation chamber, wherein a pair of cover sheets are respectively overlaid on the two sheet members so as to cover the medicinal-substance accommodation chamber;

wherein one of the sheet members and one of the cover sheets overlaid on the one of the sheet members are formed by transparent sheets and the other cover sheet has a structure capable of absorbing adverse influence causing matters, which deteriorate a medicinal substance;

wherein each of the cover sheets has a pair of lateral side ends, which extends in the direction in which the medicinal-substance accommodation chamber and the medicinal-solution accommodation chamber are arranged and each of the pair of lateral side ends of each of the cover sheets is joined to at least one of the corresponding sheet member facing each lateral side end and the opposite cover sheet protruding outward from the sheet members so as to form a first outside seal part, and each of the cover sheets has a pair of transverse ends, which extends in a direction orthogonal to the direction in which the medicinal-substance accommodation chamber and the medicinal-solution accommodation chamber are arranged, and each of the transverse ends is joined to the corresponding sheet member facing each of the transverse ends of the cover sheets so as to form a second outside seal part, thereby forming a space between the one of the cover sheets and the corresponding facing sheet member and a space between the other one of the cover sheets and the corresponding facing sheet member, respectively;

wherein an inside edge of at least a portion of the first outside seal part is located outward of an inside edge of the strong seal part defining the medicinal-substance accommodation chamber;

wherein a communication part for communication between a space on the side of the one of the cover sheets and a space on the side of the other one of the cover sheets is formed in at least a portion between the inside edge of the strong seal part and the inside edge of the first outside seal part located outward of the inside edge of the strong seal part; and wherein the communication part comprises an opening bored in the strong seal part.

2. The multi-chamber bag according to claim 1, wherein the bag body has the medicinal-solution accommodation chamber arranged on one side of the medicinal-substance accommodation chamber, an unoccupied chamber arranged on another side of the medicinal-substance accommodation chamber, and a port member that is provided adjacent to the unoccupied chamber to be in communication therewith to discharge a medicinal substance mixed with a medicinal solution;

wherein the strong seal part includes a pair of first strong seal parts that join the opposite lateral side ends of the respective sheet members together, and a pair of second strong seal parts that join the opposite transverse ends of the respective sheet members together;

wherein the weak seal part comprises two seal lines spaced apart from each other to partition the interior space into three compartments respectively serving as the medicinal-substance accommodation chamber, the medicinal-solution accommodation chamber and the unoccupied chamber;

wherein each of the cover sheets has opposite lateral side ends which extend in the direction in which the medicinal-substance accommodation chamber and the medicinal-solution accommodation chamber are arranged and each of the cover sheets is joined to at least one of the lateral side ends of the facing sheet members and the lateral side ends of the opposite cover sheet protruding outward from the sheet members; and wherein the communication part is formed between the inside edge of at least one of the first strong seal parts and the inside edge of the first outside seal part.

3. The multi-chamber bag according to claim 2, wherein the communication part comprises two communication part members respectively formed between the inside edges of the pair of first strong seal parts defining the medicinal-substance accommodation chamber and the corresponding inside edges of the pair of first outside seal parts.

4. A multi-chamber bag comprising a bag body that has a strong seal part that joins two sheet members together to define an interior space of the bag body, and a weak seal part that partitions the interior space of the bag body into a medicinal-substance accommodation chamber and a medicinal-solution accommodation chamber, wherein a pair of cover sheets are respectively overlaid on the two sheet members so as to cover the medicinal-substance accommodation chamber;

wherein the bag body has the medicinal-solution accommodation chamber arranged on one side of the medicinal-substance accommodation chamber, an unoccupied chamber arranged on another side of the medicinal-substance accommodation chamber, and a port member that is provided adjacent to the unoccupied chamber to be in communication therewith to discharge a medicinal substance mixed with a medicinal solution;

wherein the strong seal part includes a pair of first strong seal parts that join opposite lateral ends of the sheet members together, and a pair of second strong seal parts that join opposite transverse ends of the sheet members together;

wherein the weak seal part comprises two seal lines spaced apart from each other to partition the interior space into three compartments respectively serving as the medicinal-substance accommodation chamber, the medicinal-solution accommodation chamber and the unoccupied chamber;

wherein one of the sheet members and one of the cover sheets overlaid on the one of the sheet members are formed by transparent sheets, and the other cover sheet has a structure capable of absorbing adverse influence causing matters, which deteriorate a medicinal substance;

wherein each of the cover sheets has a pair of lateral side ends, which extends in the direction in which the medicinal-substance accommodation chamber and the medicinal-solution accommodation chamber are arranged and each of the pair of lateral side ends of each of the cover sheets is joined to at least one of the corresponding sheet member facing each lateral side end and the opposite cover sheet protruding outward from the sheet members so as to form a first outside seal part, and each of the cover sheets has a pair of transverse ends, which extends in a direction orthogonal to the direction in which the medicinal-substance accommodation chamber and the medicinal-solution accommodation chamber are arranged, and each of the transverse ends is joined to the corresponding sheet member facing each of the transverse ends of the cover sheets so as to form a second outside seal part, thereby forming a space between the one of the cover sheets and the corresponding facing sheet member and a space between the other one of the cover sheets and the corresponding facing sheet member, respectively, wherein an inside edge of at least a portion of the first outside seal part is located outward of an inside edge of the strong seal part defining the medicinal-substance accommodation chamber;

wherein a communication part for communication between a space on the side of the one of the cover sheets and a space on the side of the other one of the cover sheets is formed in at least a portion between the inside edge of the strong seal part and the inside edge of the first outside seal part located outward of the inside edge of the strong seal part; and wherein the communication part is formed between the inside edge of at least one of the first strong seal parts and the inside edge of the first outside seal part.

5. A multi-chamber bag comprising a hag body that has a strong seal part that joins two sheet members together to define an interior space of the bag body, and a weak seal part that partitions the interior space of the hag body into a medicinal-substance accommodation chamber and a medicinal-solution accommodation chamber, wherein a pair of cover sheets are respectively overlaid on the two sheet members so as to cover the medicinal-substance accommodation chamber;

wherein one of the sheet members and one of the cover sheets overlaid on the one of the sheet members are formed by transparent sheets and the other cover sheet has a structure capable of absorbing adverse influence causing matters, which deteriorate a medicinal substance;

wherein each of the cover sheets has a pair of lateral side ends, which extends in the direction in which the medicinal-substance accommodation chamber and the medicinal-solution accommodation chamber are arranged, and each of the pair of lateral side ends of each of the cover sheets is joined to at least one of the corresponding sheet member facing each lateral side and the opposite cover sheet protruding outward from the sheet members so as to form a first outside seal part, and each of the cover sheets has a pair of transverse ends, which extends in a direction orthogonal to the direction in which the medicinal-substance accommodation chamber and the medicinal-solution accommodation chamber are arranged, and each of the transverse ends is joined to the corresponding sheet member facing each of the transverse ends of the cover sheets so as to form a second outside seal part, thereby forming a space between the one of the cover sheets and the corresponding facing, sheet member and a space between the other one of the cover sheets and the corresponding facing sheet member, respectively;

wherein an inside edge of at least a portion of the first outside seal part is located outward of an inside edge of the strong seal part defining the medicinal-substance accommodation chamber;

wherein a communication part for communication between a space on the side of the one of the cover sheets and a space on the side of the other one of the cover sheets is formed in at least a portion between the inside edge of the strong seal part and the inside edge of the first outside seal part located outward of the inside edge of the strong seal part; and wherein the communication part comprises two communication part members respectively formed between the inside edges of the pair of first strong seal parts defining the medicinal-substance accommodation chamber and the corresponding inside edges of the pair of first outside seal parts.

6. A multi-chamber bag comprising a bag body that has a strong seal part that joins two sheet members together to define an interior space of the bag body, and a weak seal part that partitions the interior space of the bag body into a medicinal-substance accommodation chamber and a medicinal-solution accommodation chamber, wherein a pair of cover sheets are respectively overlaid on the two sheet members so as to cover the medicinal-substance accommodation chamber;

wherein one of the sheet members and one of the cover sheets overlaid on the one of the sheet members are formed by transparent sheets and the other cover sheet has a structure capable of absorbing adverse influence causing matters, which deteriorate a medicinal substance;

wherein each of the cover sheets has a pair of lateral side ends, which extends in the direction in which the medicinal-substance accommodation chamber and the medicinal-solution accommodation chamber are arranged and each of the pair of lateral side ends of each of the cover sheets is joined to at least one of the corresponding sheet member facing each lateral side end and the opposite cover sheet protruding outward from the sheet members so as to form a first outside seal part, and each of the cover sheets has a pair of transverse ends, which extends in a direction orthogonal to the direction in which the medicinal-substance accommodation chamber and the medicinal-solution accommodation chamber are arranged, and each of the transverse ends is joined to the corresponding sheet member facing each of the transverse ends of the cover sheets so as to form a second outside seal part, thereby forming a space between the one of the cover sheets and the corresponding facing sheet member and a space between the other one of the cover sheets and the corresponding facing sheet member, respectively;

wherein an inside edge of at least a portion of the first outside seal part is located outward of an inside edge of the strong seal part defining the medicinal-substance accommodation chamber;

wherein a communication part for communication between a space on the side of the one of the cover sheets and a space on the side of the other one of the cover sheets is formed in at least a portion between the inside edge of the strong seal part and the inside edge of the first outside seal part located outward of the inside edge of the strong seal part;

wherein the strong seal part is formed by joining the outer peripheral ends of the two sheet members together;

wherein the first outside seal part is formed by joining ends of the cover sheets protruding outward from the sheet members together; and wherein the communication part is formed by a gap that is defined between the outside edge of the strong seal part defining the medicinal-substance accommodation chamber and the inside edge of the first outside seal part.

* * * * *